United States Patent
Bialy et al.

(10) Patent No.: US 9,034,897 B2
(45) Date of Patent: May 19, 2015

(54) INDANYL-SUBSTITUTED 4,5,6,7-TETRA-HYDRO-1H-PYRAZOLO[4,3-C]PYRIDINES, THEIR USE AS MEDICAMENT, AND PHARMACEUTICAL PREPARATIONS COMPRISING THEM

(75) Inventors: Laurent Bialy, Kelkheim (DE); Josef Pernerstorfer, Hofheim (DE); Klaus Wirth, Kriftel (DE); Klaus Steinmeyer, Frankfurt am Main (DE); Gerhard Hessler, Hofheim (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/342,749

(22) PCT Filed: Sep. 12, 2011

(86) PCT No.: PCT/EP2011/065713
§ 371 (c)(1),
(2), (4) Date: Jul. 17, 2014

(87) PCT Pub. No.: WO2013/037389
PCT Pub. Date: Mar. 21, 2013

(65) Prior Publication Data
US 2014/0378686 A1    Dec. 25, 2014

(51) Int. Cl.
C07D 401/14    (2006.01)
A61K 31/437   (2006.01)
C07D 471/04   (2006.01)

(52) U.S. Cl.
CPC .......... *C07D 471/04* (2013.01); *A61K 31/437* (2013.01); *C07D 401/14* (2013.01)

(58) Field of Classification Search
CPC ........................... C07D 401/14; A61K 31/437
USPC .................... 546/119, 120; 514/303
See application file for complete search history.

(56) References Cited

FOREIGN PATENT DOCUMENTS

| EP | 0086422 | 8/1983 |
|---|---|---|
| WO | 2005016965 A1 | 2/2005 |
| WO | 2006136304 A1 | 12/2006 |
| WO | 2007124849 A2 | 11/2007 |
| WO | 2010025856 A1 | 3/2010 |

OTHER PUBLICATIONS

Tugusheva et al., Russian Chemical Bulletin (2006), 55(8), 1475-1486.*
The United States Department of Justice, "Former Research Chemist At Global Pharmaceutical Company Sentenced To 18 Months In Prision For Theft Of Trade Secrets" The United States Attorney's Office, District of New Jersey, http://www.justice.gov/usao/nj/Press/files/Li,%20Yuan%20Sentencing%20News%20Release.html, pp. 1-2 (May 7, 2012).
Chemical Abstracts Registry No. 1279039-15-4, entered into STN on Apr. 11, 2011.
Chemical Abstracts Registry No. 1279037-52-3, entered into STN on Apr. 12, 2011.
Chemical Abstracts Registry No. 1279036-46-2, entered into STN on Apr. 12, 2011.
Chemical Abstracts Registry No. 1279030-74-8, entered into STN on Apr. 12, 2011.
Peukert S. et al., J. Med. Chem. (2003), vol. 46, p. 486-498.
Putzke C. et al., Cardiovasc. Res. (2007), vol. 75, p. 59-68.
Roden D.M., Am. J. Cardiol. (1993), vol. 72, p. 44B-49B.
Streit A.K. et al., J. Biol. Chem. (2011), vol. 286, p. 13977-13984.
Wakili R. et al., J. Clin. Invest. (2011), vol. 121, p. 2955-2968.
Aller M.I. et al., J. Neuroscience (2005), vol. 25, p. 11455-11467.
Barth A.S. et al., Pflugers—Arch. Eur. J. Physiol. (2005), vol. 450, p. 201-208.
Bayliss D.A. et al., Respiration Physiology (2001), vol. 129, p. 159-174.
Bayliss D.A. et al., Trends Pharmacological Sciences (2008), vol. 29, p. 566-575.
Berg A.P. et al., J. Neuroscience (2004), vol. 24, p. 6693-6702.
Bittner S. et al., Brain (2009), vol. 132, p. 2501-2516.
Brundel B.J.J.M. et al., J. Am. Coll. Cardiol. (2001), vol. 37, p. 926-932.
Buckler K.J. et al., J. Physiol. (2000), vol. 525.1, p. 135-142.
Coetzee W.J. et al., Ann. New York Acad. Sci. (1999), vol. 868, p. 233-285.
Colatsky T.J. et al., Drug Dev. Res. (1990), vol. 19, p. 129-149.
Cotten J.F. et al., Anesth. Analg. (2006), vol. 102, p. 779-785.
Dalisay D.S. et al., Angew. Chem. Int. Ed. (2009), vol. 48, p. 4367-4371.

(Continued)

*Primary Examiner* — Niloofar Rahmani
(74) *Attorney, Agent, or Firm* — McDonnell Boehnen Hulbert & Berghoff LLP

(57) ABSTRACT

The invention relates to substituted 4,5,6,7-tetrahydro-1H-pyrazolo[4,3-c]pyridines of formula (I), their use as medicament, and pharmaceutical preparations comprising them. The compounds of formula (I) act on the TASK-1 potassium channel. The compounds are particularly suitable for the treatment or prevention of atrial arrhythmias, for example atrial fibrillation (AF) or atrial flutter.

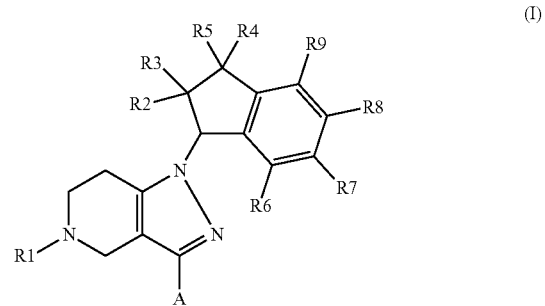

21 Claims, No Drawings

(56) References Cited

OTHER PUBLICATIONS

Dobrev D. et al., Bas. Res. Cardiol. (2003), vol. 98, p. 137-148.
Donner B.C. et al., Bas. Res. Cardiol. (2011), vol. 106, p. 75-87.
Duprat F. et al., EMBO J. (1997), vol. 16, p. 5464-5471.
Ellinghaus P. et al., J. Thorac. Cardiovasc. Surg. (2005), vol. 129, p. 1383-1390.
Flanagan M.E. et al., J. Med. Chem. (2010), vol. 53, p. 8468-8484.
Kääb S. et al., J. Mol. Med. (2004), vol. 82, p. 308-316.
Knobloch K. et al., Naunyn Schmiedeberg's Arch. Pharmacol. (2002), vol. 366, p. 482-487.
Larrow J.F. et al., Organic Syntheses (1999), vol. 76, p. 46.
Lauritzen I. et al., J. Biol. Chem. (2003), vol. 278, p. 32068-32076.
Macdonald S.J.F. et al., J. Chem. Soc. Chem., Comm. (1987), p. 1528-1530.
Mahapatra T. et al., Tetrahedron Asymmetry (2008), vol. 19, p. 1224-1232.
Maingret F. et al., EMBO J. 2001, vol. 20, p. 47-54.
Medhurst A.D. et al., Mol. Brain Res. (2001), vol. 86, p. 101-114.
Mitsunobu O. et al., Bull. Chem. Soc. Japan (1967), vol. 40, p. 2380-2382.
Miyaura N. et al., J. Chem.Soc., Chem. Comm. (1979), p. 866-867.
Patel A.J. et al., Nature Neurosci. (1999), vol. 2, p. 422-426.
Patel A.J. et al., Pflugers Arch.—Eur. J. Physiol. (2004), vol. 448, p. 261-273.
Patel A.J. et al., Trends Neurosci. (2001), vol. 24, p. 339-346.
De Lousanoff, "Extracts of No. 175 of the Roll of Deeds for 2011," CAS Search Results, pp. 1-19 Sep. 26, 2011.

\* cited by examiner

INDANYL-SUBSTITUTED 4,5,6,7-TETRA-HYDRO-1H-PYRAZOLO[4,3-C]PYRIDINES, THEIR USE AS MEDICAMENT, AND PHARMACEUTICAL PREPARATIONS COMPRISING THEM

This application is a national stage application under 35 U.S.C. §371 of International Application No. PCT/EP2011/065,713, filed Sep. 12, 2011, the disclosure of which is explicitly incorporated by reference herein.

The invention relates to 4,5,6,7-tetrahydro-1H-pyrazolo[4,3-c]pyridine compounds of the formula I,

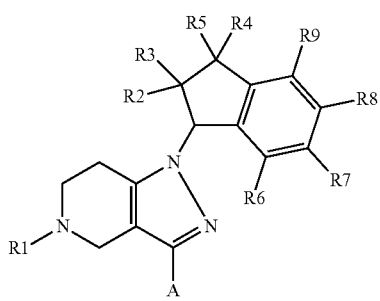

to their preparation and their use, in particular in pharmaceuticals.

The compounds of formula I act on the TASK-1 (KCNK3) potassium channel. The compounds are suitable for the treatment of several pathologies and particularly suitable as anti-arrhythmic active ingredients, in particular for the treatment and prophylaxis of atrial arrhythmias, for example atrial fibrillation (AF) or atrial flutter.

Potassium channels are widespread membrane proteins which, owing to their influences on cell membrane potentials, play an important role in many physiological processes. Within the various classes of the potassium channels, a distinction is drawn on the basis of their molecular structure between three large groups which are characterized by the number of transmembrane domains (2, 4 or 6). The group of the potassium channels with four transmembrane segments is delimited from the two others in that their representatives each have two pore domains, which is why these channels are also referred to as $K_{2P}$ channels (Coetzee W. J. et al; Molecular diversity of K+ channels; Ann. New York Acad. Sci. 1999 (868), 233-285). In functional terms, $K_{2P}$ channels are characterized in that the "leak" or "background" currents flow through them, which play an important role for the resting membrane potential and hence the excitability of nerve or muscle cells.

A family which is of particular interest among the $K_{2P}$ channels is that of the TASK channels (tandem of P domains in a weak inwardly rectifying $K^+$ channel, [TWIK]-related acid-sensitive $K^+$ channels), which include TASK-1, TASK-3, and TASK-5 subtype (D. A. Bayliss, P. Barrett, Trends in Pharmacological Sciences, 2008, 29(11), 566-575). Other terms used in the literature for the underlying genes are KCNK3 or K2P3.1 (TASK-1), KCNK9 or K2P9.1 (TASK-3) and KCNK15 or K2P15.1 (TASK-5). The greatest homology within this family is possessed by the TASK-1 and TASK-3 channels with an amino acid identity of more than 50%. Dimerization of $K_{2P}$ channels forms functional potassium channels with a total of four pore units. The streams which flow through these channels are referred to in the literature as IKso stream. In addition to a homodimerization of, for example, two TASK-1 or two TASK-3 proteins, heterodimerization of TASK-1 and TASK-3 is also possible in this context (Berg A. P., Talley E. M., Manger J. P., Bayliss D. A.; Motoneurons express Heteromeric TWIK-related acid-sensitive K+ (TASK) Channels containing TASK-1 (KCNK3) and TASK-3 (KCNK9) subunits; J. Neuroscience 2004 (24), 6693-6702).

The TASK channels are notable in particular for their very strong dependence upon the extracellular pH in the physiological range (pK ca. 6.5-7.5). The channels are inhibited at acidic pH and activated at alkaline pH. Owing to this pH dependence, the physiological function of a sensor which translates small changes in the extracellular pH to corresponding cellular signals is ascribed to the TASK channels (Duprat F., Lesage F., Fink M., Reyes R., Heurteaux C., Lazdunski M.; TASK, a human background K+ channel to sense external pH variations near physiological pH; EMBO J. 1997 (16), 5464-5471; Patel A. J., Honore E.; Properties and modulation of mammalian 2P domain K+ channels; Trends Neurosci. 2001 (24), 339-346).

TASK-1 knock-out mice show a mild phenotype and have been described and appear generally in good health and show normal breeding behavior (Journal of Neuroscience (2005), 25(49), 11455-11467).

TASK-1 is expressed in the brain and also in spinal ganglia and some peripheral tissues, for example pancreas, placenta, uterus, lung, heart, kidney, small intestine and stomach. In addition, TASK-1 has been detected in the chemosensitive cells of the brainstem and of the carotid bodies, and also the motor neurons of the hypoglossal nerve (Medhurst A. D., Rennie G., Chapman C. G., Meadows H., Duckworth M. D., Kelsell R. E., Glober I. I., Pangalos M. N.; Distribution analysis of human two pore domain potassium channels in tissues of the central nervous system and periphery; Mol. Brain Res. 2001 (86), 101-114).

Electrical currents which are caused by TASK-1 potassium channels have been detected in motor neurons of the hypoglossal nerve, a motor cranial nerve which possesses the most important function for the maintenance and patency of the upper respiratory pathways, and locus coeruleus. It has been found that TASK-1 channels are involved in respiratory regulation in respiratory neurons of the brainstem, in carotid bodies and in motor neurons of the hypoglossal nerve, and also in neuroepithelial cells of the lung. In the event of inadequate respiration (hypoxia, hindered breathing) and in the event of physical stress, either via a rise in the $CO_2$ concentration and the resulting acidosis or via acidic metabolites, there is a lowering of the pH and hence a blockage of the pH-dependent TASK-1 channels. This depolarizes the cells, which leads to the activation of the neurons involved in the respiratory regulation (Buckler K. J., Williams B. A., Honore E.; An oxygen-, acid- and anaesthetic-sensitive TASK-like background potassium channel in rat arterial chemoreceptor cells; J. Physiol. 2000 (525), 135-142; Bayliss D. A., Talley E. M., Sirois J. E., Lei Q.; TASK-1 is a highly modulated pH-sensitive 'leak' K+ channel expressed in brainstem respiratory neurons; Respiration Physiology 2001 (129), 159-174).

An increase in the activity of chemosensitive neurons in conjunction with an activation of the motor neurons of the hypoglossal nerve through blockage of the TASK-1 channel can stimulate respiration and simultaneously stabilize the upper airways to protect them from collapse and occlusion. Moreover, snoring can be inhibited by stabilizing the upper airway via an increase in pharyngeal muscle activity. The blockage of the TASK-1 ion channels is therefore useful in the treatment of respiratory disorders, for example of sleep apnea (Brendel, J.; Goegelein, H.; Wirth, K.; Kamm, W., WO2007124849).

In cultivated granulosa cells of the cerebellum, it has been shown that genetic inactivation of TASK channels brings about neuroprotective action (Lauritzen I., Zanzouri M., Honoré E., Duprat F., Ehrengruber M. U., Lazdunski M., Patel A. J.; $K^+$-dependent cerebellar granule neuron apoptosis—Role of Task leak $K^+$ channels; J. Biol. Chem. 2003 (278), 32068-32076). It has also been shown that TASK-1 channels are responsible for programmed cell death (apoptosis) in granulosa cells, and that the cell death can be prevented by blocking the TASK-3. Thus, the development of specific inhibitors of the TASK-1/3 channels can be useful for the treatment of neurodegenerative disorders (Patel A. J., Lazdunski M., The 2P-domain $K^+$ channels: role in apoptosis and tumorigenesis, Pflugers Arch. 2004 (448), 261-273).

It has been stated that TASK-1 is relevant for setting the resting membrane potential and balancing neuronal excitability that is expressed on T cells and neurons, and is a key modulator of T cell immunity and neurodegeneration in autoimmune central nervous system inflammation. After induction of experimental autoimmune encephalomyelitis, an experimental model mimicking multiple sclerosis, TASK1 (−/−) mice showed a significantly reduced clinical severity and markedly reduced axonal degeneration compared with wild-type controls. T cells from TASK1(−/−) mice displayed impaired T cell proliferation and cytokine production, while the immune repertoire is otherwise normal. In addition to these effects on systemic T cell responses, TASK1 exhibits an independent neuroprotective effect which was demonstrated using both a model of acutely prepared brain slices cocultured with activated T cells as well as in vitro cultivation experiments with isolated optic nerves. Preventive blockade of TASK1 significantly ameliorated experimental autoimmune encephalomyelitis after immunization and significantly reduced disease severity and was capable of lowering progressive loss of brain parenchymal volume as assessed by magnetic resonance imaging. Thus TASK-1 blockers are potent compounds useful for the therapy of inflammatory and degenerative central nervous system disorders (Bittner Stefan; Meuth Sven G; Gobel Kerstin; Melzer Nico; Herrmann Alexander M; Simon Ole J; Weishaupt Andreas; Budde Thomas; Bayliss Douglas A; Bendszus Martin; Wiendl Heinz, Brain: a journal of neurology (2009), 132 (Pt 9), 2501-16).

TASK-1, a member of two-pore-domain (K2P) potassium channel family, has emerged as a target for the pharmacological treatment of atrial fibrillation recently. Two-pore-domain (K2P) potassium channels mediate background potassium currents, stabilizing resting membrane potential and expediting action potential repolarization. In the heart, TASK-1 channels have been shown to play a role in cardiac repolarization, (Basic Res Cardiol. 2011 January; 106(1):75-87, Putzke C, WemhÖner K, Sachse F B, Rinné S, SchlichthÖrl G, Li X T, Jaé L, Eckhardt I, Wischmeyer E, Wulf H, Preisig-Müller R, Daut J, Decher N (2007), Cardiovascular Research, 75: 59-68).

Atrial fibrillation (AF) and atrial flutter are extremely common cardiac rhythm disorder that causes substantial morbidity and contributes to mortality (Journal of Clinical Invest. 2011; 121(8):2955-2968). Presently available therapeutic approaches have major limitations, including limited efficacy and potentially serious side effects such as malignant ventricular arrhythmia induction or negative inotropic effects. The occurrence of AF increases with age and frequently leads to fatal sequelae such as stroke. The class I and III antiarrhythmics in use at present reduce the rate of recurrence of AF but are used to only a limited extent because of their potential proarrhythmic side effects and limited efficacy. The growing incidence of AF emphasizes the importance of identifying appropriate treatments, particularly drugs, that are safe, effective, and associated with improved clinical outcomes.

It has been shown that in atrial fibrillation and flutter re-entrant mechanism play an important role in the induction and maintenance of the arrhythmia. Such reentries or re-entrant waves occur when the cardiac tissue has a low conduction velocity and, at the same time, short refractory periods. Increasing the myocardial refractory period by prolonging the action potential is an acknowledged mechanism for terminating arrhythmias or for preventing them to develop (T. J. Colatsky et al., Drug Dev. Res. 19, 1990, 129-140; "Potassium channels as targets for antiarrhythmic drug action"). The length of the action potential is essentially determined by the extent of repolarizing $K^+$ currents which flow out of the cells through various $K^+$ channels. TASK-1 constitutes one of those repolarizing potassium currents. Its inhibition prolong the action potential and thereby refractoriness.

Most of the known class III antiarrhythmics (e.g. dofetilide, E4031 and d-sotalol) block predominantly or exclusively the rapidly activating potassium channel $IK_r$, which can be detected both in cells of the human ventricle and in the atrium. It has emerged that these compounds have an increased proarrhythmic risk at heart rates which are low or normal, and arrhythmias referred to as torsades de pointesi have been observed in particular (D. M. Roden, Am. J. Cardiol. 72, 1993, 44B-49B; "Current status of class III antiarrhythmic drug therapy"). Apart from this proarrhythmic risk, the therapeutic efficacy of the $I_{Kr}$ blockers has been found to decline under the conditions of tachycardia (electrical tachycardic atrial remodelling).

TASK-1 expression in the human heart has been shown to be restricted to the atria with no or very little expression in the ventricles. A further advantage is that TASK-1 expression is not decreased but even slightly increased in atrial fibrillation patients compared with sinus rhythm patients, by contrast a decreased expression of other atrial $K^+$ channels has been reported in atrial fibrillation patients compared with sinus rhythm patients: see for example Basic. Res. Cardiol. 2003, 98, 137-148, JACC Vol. 37, No. 3, 2001). Thus, TASK-1 is still expressed in the target patient population (Journal of Molecular Medicine 2004, 308-316; European Journal of Physiology 2005, 450, 201-208, WO 2005/016965; Journal of Thoracic and Cardiovascular Surgery 2005).

In spite of the great physiological significance of the TASK channels, only very few pharmacological modulators of these channels are known to date in the literature. It has been stated that an activation of the TASK-1 channel can be achieved by therapeutic concentrations of the inhalative anesthetics halothane and isoflurane (Patel A. J., Honoré E., Lesage F., Fink M., Romey G., Lazdunski M.; Inhalational anesthetics activate two-pore-domain background K+ channels; Nature Neurosci. 1999 (2), 422-426). Furthermore, some Kv1.5 blockers which also inhibit the TASK-1 channel are described in the state of the art (Brendel, J.; Goegelein, H.; Wirth, K.; Kamm, W., WO2007124849, Brendel, J.; Englert, H. C.; Wirth, K.; Wagner, M.; Ruxer, J.-M.; Pilorge, F., WO2006136304). A1899, a previously described Kv1.5 blocker (Peukert, S., Brendel, J., Pirard, B., Brueggemann, A., Below, P., Kleemann, H.-W., Hemmerle, H., Schmidt, W.; Identification, Synthesis, and Activity of Novel Blockers of the Voltage-Gated Potassium Channel Kv1.5.; Journal of Medicinal Chemistry (2003), 46(4), 486-498) has been stated to be a TASK-1 blocker (Streit, A. K.; Netter, M. F., Kempf, F., Walecki, M., Rinne, S., Bollepalli, M. K.; Preisig-Mueller, R.; Renigunta, V.; Daut, J.; Baukrowitz, T.; Sansom, M. S. P.; Stansfeld, P. J.; Decher, N. A Specific Two-pore Domain Potassium Channel Blocker Defines the Structure of the TASK-1 Open Pore; Journal of Biological Chemistry (2011), 286(16), 13977-13984). Also arachidonamide anandamide (an endogenous ligand of the cannabinoid receptor) and its methanandamide homolog have been described as TASK-1 blockers (Maingret F., Patel A. J., Lazdunski M., Honoré E.; The endocannabinoid anandamide is a direct and selective blocker of the background K+ channel TASK-1; EMBO J. 2001 (20), 47-54). Doxapram, which is used for the treatment of respiratory disorders has been stated to be a TASK-1 blocker (Cotten J. F., Keshavaprasad B., Lasteri M. J., Eger E. I., Yost C. S.; The Ventilatory Stimulant Doxapram Inhibits TASK Tandem Pore ($K_{2P}$) Potassium Channel Function but Does Not Affect Minimum Alveolar Anesthetic Concentration; Anesth. Analg. 2006 (102) 779-785).

Thus, a goal of the present invention is to provide efficient TASK-1 inhibitors suitable for the treatment and prevention of TASK-1 related conditions. The present invention relates to TASK-1 blockers of the formula I

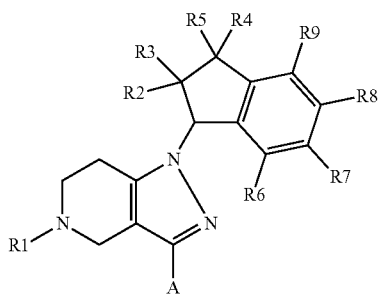

wherein
A=$(C_6-C_{10})$-aryl or five-membered or six-membered heteroaryl, comprising 1-3 heteroatoms selected from the group N, O and S,
  wherein aryl and heteroaryl are optionally substituted with 1-3 substituents selected independently from F, Cl, Br, $(C_1-C_6)$-alkyl, $(C_1-C_6)$-alkyloxy-, $C_6)$-alkyl-S—, NC—, $(C_1-C_6)$-alkyl-OC(O)—, $(C_1-C_6)$-alkyloxy-$(C_1-C_6)$-alkyl- or $R^{12}R^{13}N$—C(O)—,
    wherein one or more hydrogen atoms of the alkyl moieties may be replaced by fluorine;
R1=$R^{10}$—C(O)—, $(C_3-C_6)$-cycloalkyl, $(C_1-C_6)$-alkyl-$SO_2$— or $R^{12}R^{13}N$—C(O)—$(C_1-C_6)$-alkyl-,
  wherein one or more hydrogen atoms of the alkyl moieties may be replaced by fluorine;
R2=H, OH, $(C_1-C_6)$-alkyl, $(C_1-C_6)$-alkyloxy-, $(C_1-C_6)$-alkyl-C(O)O—;
R3=H, $(C_1-C_6)$-alkyl;
R4=H, F, $(C_1-C_6)$-alkyl, wherein one or more hydrogen atoms of the alkyl residue may be replaced by fluorine;
R5=H, F, $(C_1-C_6)$-alkyl, wherein one or more hydrogen atoms of the alkyl residue may be replaced by fluorine;
R6 to R9 are each independently selected from H, F, Cl, Br, NC—, $(C_1-C_6)$-alkyl, $(C_3-C_6)$-cycloalkyl, $(C_1-C_6)$-alkyl-OC(O)—, $(C_1-C_6)$-alkyloxy-,
  wherein one or more hydrogen atoms of the alkyl moieties may be replaced by fluorine;
R10=H, $(C_3-C_6)$-cycloalkyl, $(C_1-C_6)$-alkyloxy-, HO—$(C_1-C_6)$-alkyl-$(C_3-C_6)$-cycloalkyl-$(C_1-C_6)$-alkyl- or $R^{12}R^{13}N$—,
  wherein one or more hydrogen of the alkyl moieties may be replaced by fluorine, and
R11=H, $(C_3-C_6)$-cycloalkyl, OH, $(C_1-C_6)$-alkyloxy- or $(C_1-C_6)$-alkyl-S—,
  wherein one or more hydrogen of the alkyl moieties may be replaced by fluorine;
R12 and R13 are each independently H or $(C_1-C_6)$-alkyl;
and/or of a stereoisomeric form of the compound of the formula I and/or mixtures of these forms, and/or a physiologically tolerated salt of the compounds of formula I.

Particularly suitable compounds are compounds of formula I, wherein
A=phenyl, furanyl, furazanyl, imidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, pyrazinyl, pyrazolinyl, pyrazolyl, pyridazinyl, pyridyl, pyrimidinyl, pyrrolyl, 1,2,3-thiadiazolyl, 1,2,4-thiadiazolyl, 1,2,5-thiadiazolyl, 1,3,4-thiadiazolyl, thiazolyl, thiophenyl, triazinyl, 1,2,3-triazolyl, 1,2,4-triazolyl, 1,2,5-triazolyl, or 1,3,4-triazolyl radicals,
  optionally substituted with 1, 2 or 3 residues selected independently from F, Cl, $(C_1-C_4)$-alkyloxy-, $(C_1-C_4)$-alkyl-OC(O)—, $(C_1-C_4)$-alkyl-$SO_2$—, NC—,
    wherein one or more hydrogen atoms of the alkyl moieties may be replaced by fluorine;
R1=$R^{10}$—C(O)—, $R^{11}$—$(C_1-C_4)$-alkyl, $(C_3-C_6)$-cycloalkyl, or $(C_1-C_2)$-alkyl-$SO_2$—;
R2=H, OH, $(C_1-C_4)$-alkyloxy- or $(C_1-C_4)$-alkyl-C(O)O—;
R3=H, $(C_1-C_6)$-alkyl;
R4=H, F, $(C_1-C_6)$-alkyl, wherein one or more hydrogen atoms of the alkyl residue may be replaced by fluorine;
R5=H, F, $(C_1-C_6)$-alkyl, wherein one or more hydrogen atoms of the alkyl residue may be replaced by fluorine;
R6 to R9 are each independently selected from H, F, Cl, Br, NC—, $(C_1-C_4)$-alkyl, cyclopropyl, $(C_1-C_4)$-alkyl-OC(O)—, $(C_1-C_4)$-alkyloxy-, $C_4)$-alkyl-S—;
  wherein one or more hydrogen atoms of the alkyl moieties may be replaced by fluorine;
R10=cyclopropyl, $(C_1-C_4)$-alkyloxy-, cyclopropyl-$(C_1-C_4)$-alkyl-, $R^{12}R^{13}N$—;
R11=H, cyclopropyl, OH, $(C_1-C_4)$-alkyloxy-,
  wherein one or more hydrogen of the alkyl moieties may be replaced by fluorine;
R12 and R13 are each independently H or $(C_1-C_4)$-alkyl;
and/or of a stereoisomeric form of the compound of the formula I and/or mixtures of these forms, and/or a physiologically tolerated salt of the compounds of formula I.

Preferred compounds are compounds of formula I, wherein
A=phenyl, pyridyl, pyrazinyl, pyridazinyl, pyrimidinyl, pyrazolyl, imidazolyl, isothiazolyl, thiazolyl, or thiophenyl radicals,
  optionally substituted with 1, 2 or 3 residues selected independently from F, Cl, methoxy, ethoxy, methyl, ethyl, NC—, $CF_3O$—, $CF_3$;
R1=$R^{10}$—C(O)—, $R^{11}$—$(C_1-C_4)$-alkyl- or $CH_3$—$SO_2$—;
R2=OH, methoxy, ethoxy, methyl-C(O)O—, ethyl-C(O)O—;
R3=H, methyl
R4, R5=H
R6 to R9 are each independently selected from H, F, Cl, Br, NC—, methyl, ethyl, cyclopropyl, methoxy, ethoxy, methyl-S—, ethyl-S—, $CF_3$;
R10=methyl, ethyl, n-propyl, isopropyl, n-butyl, isobutyl, sec-butyl, tert-butyl, cyclopropyl, methoxy, ethoxy, $(C_1-C_2)$-alkyl-O—$(C_1-C_2)$-alkyl, cyclopropyl-$(C_1-C_2)$-alkyl-, $R^{12}R^{13}N$—;

R11=H, cyclopropyl, methoxy, ethoxy, $CF_3$; and
R12 and R13 are each independently H, methyl or ethyl;
and/or of a stereoisomeric form of the compound of the formula I and/or mixtures of these forms, and/or a physiologically tolerated salt of the compounds of formula I.

Particularly preferred are compound according to formula I, wherein
A=phenyl, pyridyl, isothiazolyl, thiazolyl, or thiophenyl radicals,
  optionally substituted with 1 or 2 residues selected independently from F, Cl, methoxy, methyl, NC—, $CF_3O$—, $CF_3$;
R1=$R^{10}$—C(O)—, $R^{11}$—$(C_nH_{2n})$—, isopropyl, tert-butyl or $CH_3$—$SO_2$—,
  wherein n=1, 2 or 3; R2=OH, methoxy;
R3=H, methyl;
R4, R5, R6=H;
R7, R8 are independently selected from H, F, Cl, Br;
R9=H, F, Cl, Br, NC—, methyl, ethyl, cyclopropyl, methoxy, ethoxy, methyl-S—, ethyl-S— or $CF_3$;
R10=methyl, ethyl, n-propyl, isopropyl, n-butyl, isobutyl, tert-butyl, cyclopropyl, methoxy, methoxymethyl-; and
R11=H, cyclopropyl, methoxy, $CF_3$;
and/or of a stereoisomeric form of the compound of the formula I and/or mixtures of these forms, and/or a physiologically tolerated salt of the compounds of formula I.

A further embodiment describes compounds of the formula I in which A is phenyl, 2-pyridyl, 3-pyridyl, 4-pyridyl, 2-thiophenyl, 3-thiophenyl, 2-pyrimidinyl, 4-pyrimidinyl, 5-pyrimidinyl, 2-pyrazinyl, 3-pyridazinyl, 4-pyridazinyl, 3-pyrazolyl, 4-pyrazolyl, 2-imidazolyl, 4-imidazolyl, 2-thiazolyl, 4-thiazolyl, 5-thiazolyl, 3-isothiazolyl, 4-isothiazolyl, 5-isothiazolyl, where each of the aryl radicals, for example phenyl, is unsubstituted or substituted with 1, 2 or 3 residues selected independently from F, Cl, $(C_1-C_4)$-alkyloxy-, $(C_1-C_4)$-alkyl-OC(O)—, $SO_2$—, NC—, wherein one or more hydrogen atoms of the alkyl moieties may be replaced by fluorine. Preferred substituents of the group A are F, Cl, methoxy, ethoxy, methyl, ethyl, NC—, $CF_3O$—, $CF_3$.

Alkyl radicals have between 1 and 6, preferably between 1 and 4 carbon atoms and may be straight-chain or branched. Alkyl radicals may also be straight-chain or branched if they are substituted or are present in other radicals, for example in an alkyloxy radical (alkoxy radical) or in a fluorinated alkyl radical. Examples of alkyl radicals are methyl, ethyl, n-propyl, isopropyl, n-butyl, isobutyl, sec-butyl and tert-butyl. One or more, for example 1, 2, 3, 4, 5, 6, 7, 8, or 9 hydrogen atoms in alkyl radicals may be replaced by fluorine atoms. Preferred fluorinated alkyl radicals are $CF_3$, $CF_2H$ and $CFH_2$. Substituted alkyl radicals may be substituted in any positions. Preferred alkyloxy radicals are methoxy and ethoxy. These explanations with respect to alkyl radicals apply correspondingly to alkyl radicals which in the definition of a group in the compounds of the formula I are bonded to two adjacent groups, or linked to two groups, and may be regarded as divalent alkyl radicals (alkanediyl radicals, alkylene radicals), like in the case of the alkyl part of a substituted alkyl group, for example the group $(C_1-C_6)$-alkyloxy-$(C_1-C_6)$-alkyl- or the group $R^{11}$—$(C_1-C_6)$-alkyl-, in which groups and likewise in other groups the terminal hyphen denotes the free bond via which the group is bonded, and thus indicates via which subgroup a group composed of subgroups is bonded. Thus, such radicals can also be straight-chain or branched, the bonds to the adjacent groups can be located in any positions and can start from the same carbon atom or from different carbon atoms, and they can be unsubstituted or substituted by fluorine substituents independently of any other substituents. Examples of such divalent alkyl radicals are methylene, 1,1-ethylene, 1,2-ethylene, 1,1-propylene, 1,2-propylene, 2,2-propylene, 1,3-propylene, 1,1-butylene, 1,4-butylene, etc.

Examples of cycloalkyl radicals having 3 to 6 C atoms are cyclopropyl, cyclobutyl, 1-methylcyclopropyl-, 2-methylcyclopropyl-, cyclobutyl, 2-methylcyclobutyl-, 3-methylcyclobutyl-, cyclopentyl, 2-methylcyclopentyl-, 3-methylcyclopentyl-, cyclohexyl etc.

Preferred heteroaryl residues are five or six-membered rings, comprising 1 to 3 heteroatoms selected from the group N, O and S, wherein a heteroaryl ring preferably comprise only one O or S atom. Preferred heteroaryl groups are 2-thiophenyl, 3-thiophenyl, 2-pyrimidinyl, 4-pyrimidinyl, 5-pyrimidinyl, 2-pyrazinyl, 3-pyridazinyl, 4-pyridazinyl, 3-pyrazolyl, 4-pyrazolyl, 2-imidazolyl, 4-imidazolyl, 2-thiazolyl, 4-thiazolyl, 5-thiazolyl, 3-isothiazolyl, 4-isothiazolyl, 5-isothiazolyl, wherein particularly preferred are 2-pyridyl, 3-pyridyl and 4-pyridyl. The heteroaryl residues may unsubstituted or substituted with one or two substituents. Preferred substituents of the heteroaryl residues are F, Cl, methoxy, ethoxy, methyl, ethyl, NC—, $CF_3O$—, $CF_3$.

A preferred aryl residue is phenyl, wherein one or two hydrogen may be replaced by substituents, preferably selected from the group F, Cl, methoxy, ethoxy, methyl, ethyl, NC—, $CF_3O$—, $CF_3$.

If a radical is disubstituted or trisubstituted, the substituents may be identical or different.

If the compounds of the formula I comprise one or more basic groups or one or more basic heterocycles, the invention also includes the corresponding physiologically acceptable salts including trifluoroacetates, in particular the pharmaceutically acceptable salts. Thus, the compounds of the formula I which have one or more basic, i.e. protonatable, groups or comprise one or more basic heterocyclic rings, can also be used in the form of their physiologically tolerated acid addition salts with inorganic or organic acids, for example as hydrochlorides, phosphates, sulfates, methanesulfonates, acetates, lactates, maleates, fumarates, malates, gluconates etc. Salts can be obtained from compounds of the formula I by conventional processes, for example by combining with an acid in a solvent or dispersant or else by anion exchange from other salts. The compounds of the formula I may also be deprotonated on an acidic group and be used for example as alkali metal salts, preferably sodium or potassium salts, or as ammonium salts, for example as salts with ammonia or organic amines or amino acids.

In a further embodiment of the present invention compounds of general formula I as described above are covered by the present application, with the proviso that 1-[1-((1R,2R)-4,6-Difluoro-2-hydroxy-indan-1-yl)-3-(2-fluoro-5-methoxy-phenyl)-1,4,6,7-tetrahydro-pyrazolo[4,3-c]pyridin-5-yl]-ethanone; 1-[1-((1S,2S)-4,6-Difluoro-2-hydroxy-indan-1-yl)-3-(3-trifluoromethoxy-phenyl)-1,4,6,7-tetrahydro-pyrazolo[4,3-c]pyridin-5-yl]-ethanone; 3-[5-Acetyl-1-((1R,2R)-4,6-difluoro-2-methoxy-indan-1-yl)-4,5,6,7-tetrahydro-1H-pyrazolo[4,3-c]pyridin-3-yl]-benzonitrile and 1-[1-((1R,2R)-4,6-Difluoro-2-methoxy-indan-1-yl)-3-(4-fluoro-phenyl)-1,4,6,7-tetrahydro-pyrazolo[4,3-c]pyridin-5-yl]-ethanone are not encompassed.

Particularly preferred are compounds of formula I, wherein,
A=phenyl substituted a residue selected from Cl, NC—, or $CF_3$, preferably in the meta-position;
R1=R10-C(O)—;
R2=OH;
R3, R4, R5, R6 and R8=H;
R7, R9 are independently selected from F and Cl; and R10=methyl, ethyl, isopropyl, cyclopropyl;
and/or of a stereoisomeric form of the compound of the formula I and/or mixtures of these forms, and/or a physiologically tolerated salt of the compounds of formula I.

The compounds of the formula I may exist in stereoisomeric forms. The centers of asymmetry which are present may independently of one another have the S configuration or the R configuration. The invention includes all possible stereoisomers, for example enantiomers or diastereomers, and mixtures of two or more stereoisomeric forms, for example enantiomers and/or diastereomers, in any ratios. The invention thus includes for example enantiomers in enantiopure form, both as levorotatory and as dextrorotatory antipodes, and in the form of mixtures of the two enantiomers in various ratios or in the form of racemates. Individual stereoisomers can be prepared as desired by fractionating a mixture by conventional methods or for example by stereoselective synthesis.

In a preferred embodiment the 1,4,6,7-tetrahydro-pyrazolo [4,3-c]pyridine moiety in compounds of formula I and the residue R2 have preferably trans configuration in compounds of formula I.

For the preparation of the compounds of formula I the following methods can be used.

In the described various chemical processes, the residues R1, R2, R3, R6, R7, R8, R9 and A have the same meaning as in compounds of the formula I, provided that no specific definition of the respective residue is mentioned. In the following reaction schemes the residues R4 and R5 are hydrogen atoms. However, these reactions can be carried out analogously with compounds, wherein R4 and R5 have an above-mentioned meaning other than hydrogen.

The preparation of diverse 4,5,6,7-tetrahydro-1H-pyrazolo [4,3-c]pyridine intermediates can be done according to Scheme 1 (Method A) following a previously described synthesis (EP 0 086 422 A2). The synthesis is applicable to a large variety of different groups A. Thus, starting from commercially available 1-acetyl-4-piperidone 1-(4-Morpholin-4-yl-3,6-dihydro-2H-pyridin-1-yl)-ethanone (enamine 1) is obtained. Therefore, morpholine is added to a solution of 1-acetyl-4-piperidone in the presence of p-toluenesulfonic acid monohydrate (catalytic PTSA). After acylation with commercially available acyl chlorides, followed by acidic aqueous hydrolysis the diketones 2 are obtained and can be subjected to ring-closure with hydrazine hydrate to give the corresponding diverse 4,5,6,7-tetrahydro-1H-pyrazolo[4,3-c]pyridine intermediates 3.

Scheme 1

Method A

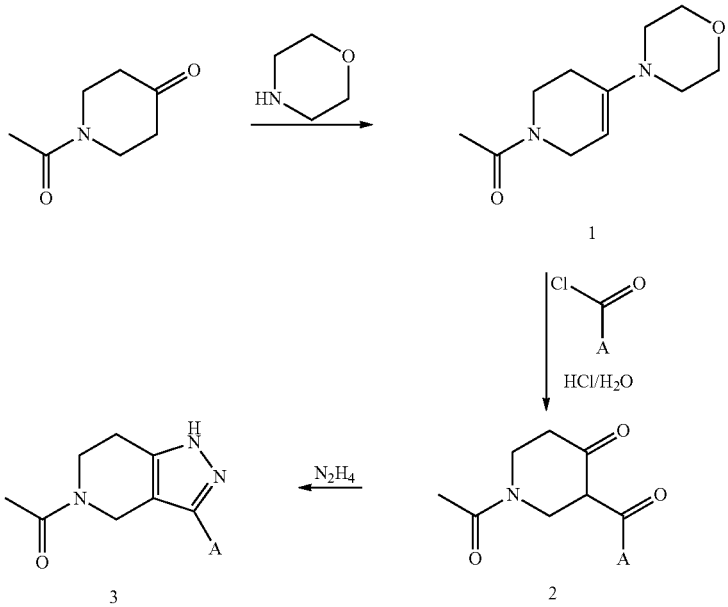

Method B

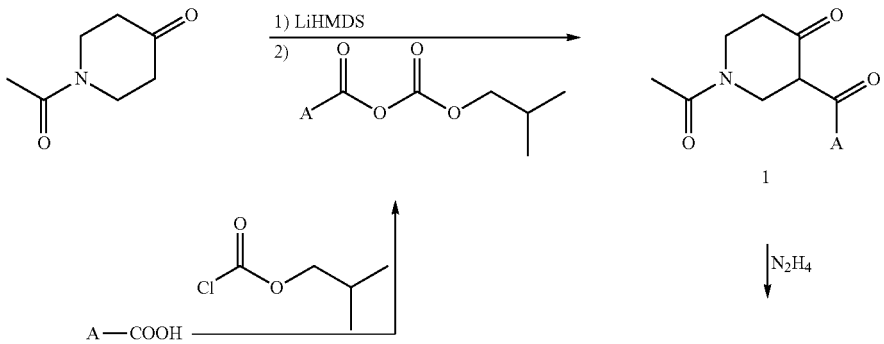

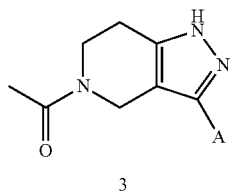

3

The acyl chlorides can alternatively be prepared by standard procedures from the corresponding acids e.g. by reaction with thionyl chloride in the presence of catalytic amounts of DMF (see for example Dalisay, D. S.; Quach, T.; Nicholas, G. N.; Molinski, T. F., Angewandte Chemie, International Edition, 2009, vol. 48, 4367-4371). If A is a heteroaryl than sometimes an alternative synthesis is preferable and can be used as shown in Scheme 1 (method B). Thus starting from commercially available acids the mixed anhydrides are formed by reaction with isobutylchloroformate. 1-Acetyl-4-piperidone 1-(4-Morpholin-4-yl-3,6-dihydro-2H-pyridin-1-yl)-ethanone can be deprotonated with strong bases like lithium hexamethyldisilazide and reacted with the mixed anhydride described above. The diketones 2 are obtained and can be subjected to ring-closure with hydrazine hydrate to give the corresponding diverse 4,5,6,7-tetrahydro-1H-pyrazolo[4,3-c]pyridine intermediates 3.

The second intermediates needed in the synthesis of the described TASK-1 blockers can be obtained by epoxidation of various substituted indenes 5 as shown in Scheme 2 by following a reaction sequence as published before (WO 2010/025856, particularly on page 114-117). The indenes can be either purchased commercially or synthesized in a short sequence starting from indan-1-ones. Thus reduction with sodium borohydride yields in the corresponding indan-1-ols 4. After elimination of water for example by heating in toluene in the presence of a catalytic amount of para-toluene sulfonic acid monohydrate gives the corresponding indenes 5. The epoxidation can be performed in an enantioselective manner according to reaction steps A or B in Scheme 2 by using the Jacobsen catalyst which is commercially available (Larrow, Jay F.; Roberts, Ed; Verhoeven, Thomas R.; Ryan, Ken M.; Senanayake, Chris H.; Reider, Paul J.; Jacobsen, Eric N., Organic Syntheses (1999), 76). For reaction step A a (S,S)-Jacobsen catalyst, for reaction B a (R,R)-Jacobsen catalyst is used together with 4-(3-phenylpropyl)pyridine N-oxide. Alternatively the racemic epoxides can be obtained by using meta-chloroperbenzoic acid as reagent (reaction step C). Another approach is the 2 step oxidation with N-bromosuccinimide followed by elimination of HBr with NaOH (reaction step D).

Another set of intermediates can be obtained by alkylation of indan-1-ones as shown in Scheme 3 (according to Mahapatra, Tridib; Jana, Nandan; Nanda, S, Tetrahedron: Asymmetry (2008), 19(10), 1224-1232). For example after deprotonation with a strong base like lithium diisopropylamide and reaction with electrophiles like alkyl halogenides e.g. of the formula R31, substituted derivatives 7 are available. After reduction to substituted 2-alkyl-indan-1-ols 8 with sodium borohydride and elimination by heating in toluene, 2-alkyl-1H-indenes 9 are obtained in the presence of a catalytic amount of para-toluene sulfonic acid monohydrate which can be submitted to diverse epoxidation procedures as described above to give epoxides 10. For the preparation of racemic epoxides particularly the addition of meta-chloroperbenzoic acid as reagent is suitable.

Scheme 2

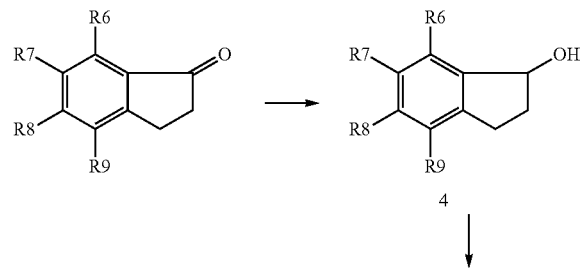

Scheme 3

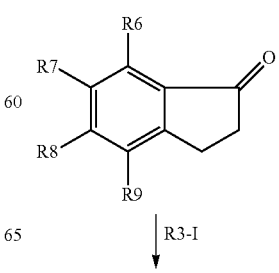

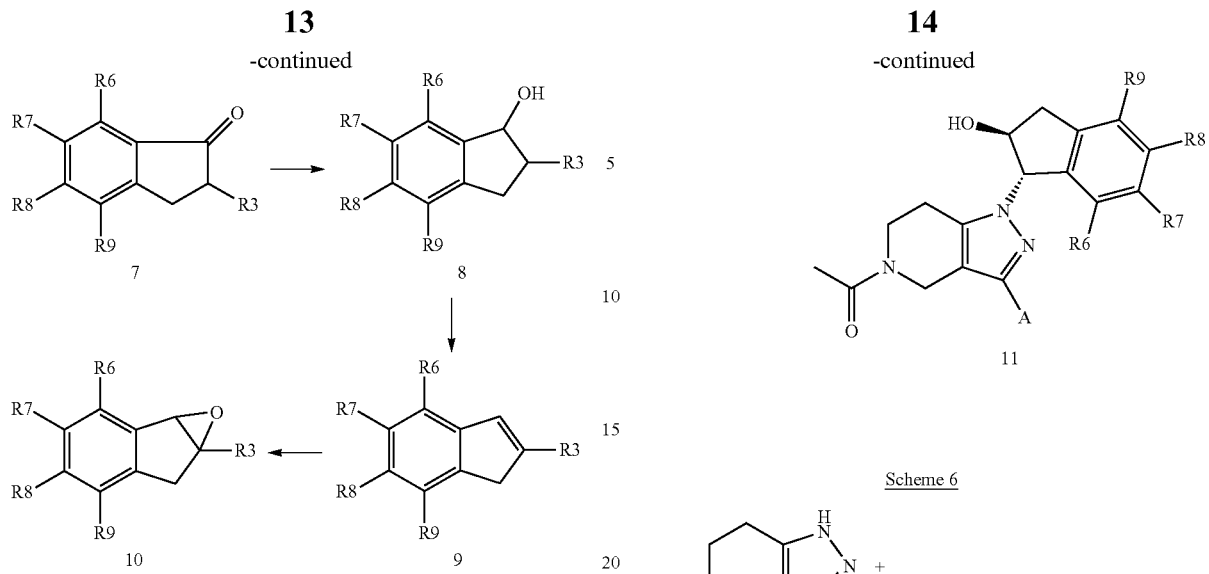

It has been found that 4,5,6,7-tetrahydro-1H-pyrazolo[4,3-c]pyridine intermediates 3 can successfully be reacted with epoxides described above to give 2-hydroxy-indan-1-yl-substituted 4,5,6,7-tetrahydro-1H-pyrazolo[4,3-c]pyridines 11 as shown in Schemes 4-6. Thus, by heating a mixture of the 4,5,6,7-tetrahydro-1H-pyrazolo[4,3-c]pyridine intermediates 3 and the epoxides 6 in the presence of an excess of a base, for example $K_2CO_3$ in an inert solvent like $CH_3CN$ the compounds 11 can be obtained. Alternatively it is possible to deprotonate compounds 3 with strong bases like NaH and alkylate them with the epoxides 6.

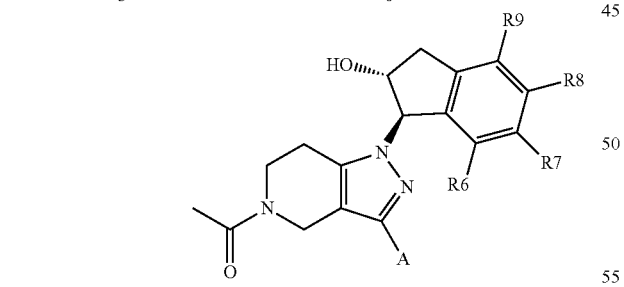

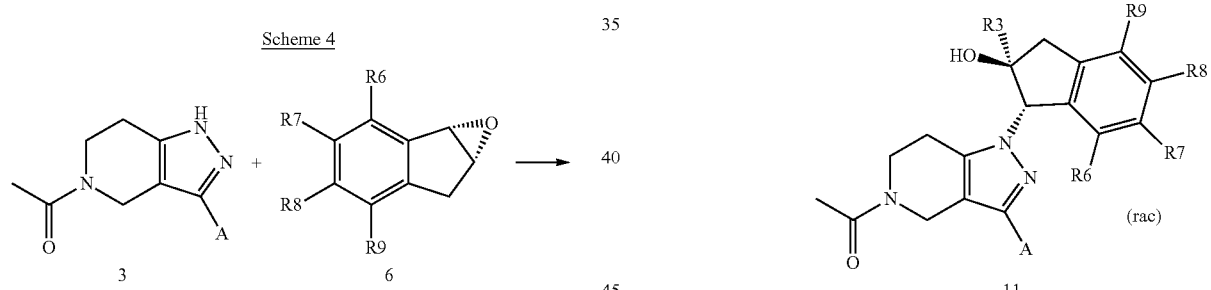

It has further been found that 4,5,6,7-tetrahydro-1H-pyrazolo[4,3-c]pyridine intermediates 3 can successfully be reacted in a "Mitsunobu-type" reaction (Bull. Chem. Soc. Japan 1967, 40, 2380-2382) with aminoindan-1-ols 4'/8' as shown in Scheme 7. Thus by heating a mixture of the 4,5,6,7-tetrahydro-1H-pyrazolo[4,3-c]pyridine intermediates 3 and the aminoindan-1-ols 4'/8' in the presence of a phosphine like trin-butylphosphine and 1,1'-(azodicarbonyl) compounds like 1,1'-(azodicarbonyl)dipiperidine the corresponding potent TASK-1 blockers 12 were obtained. The definition of residue R2 in compounds 4' and 8' utilized in the reaction does preferably comprise no hydroxyl group. Preferably R2 is H or a $(C_1-C_6)$-alkyl, $(C_1-C_6)$-alkyloxy, $(C_1-C_6)$-alkyl-C(O)O— group. Compound 4' and 8', wherein R2 is a $(C_1-C_6)$-alkyloxy or $(C_1-C_6)$-alkyl-C(O)O— group can be prepared analogously to Scheme 2 and 3.

Scheme 7

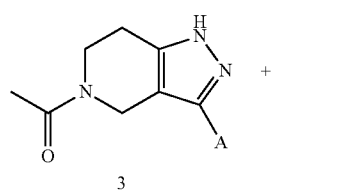

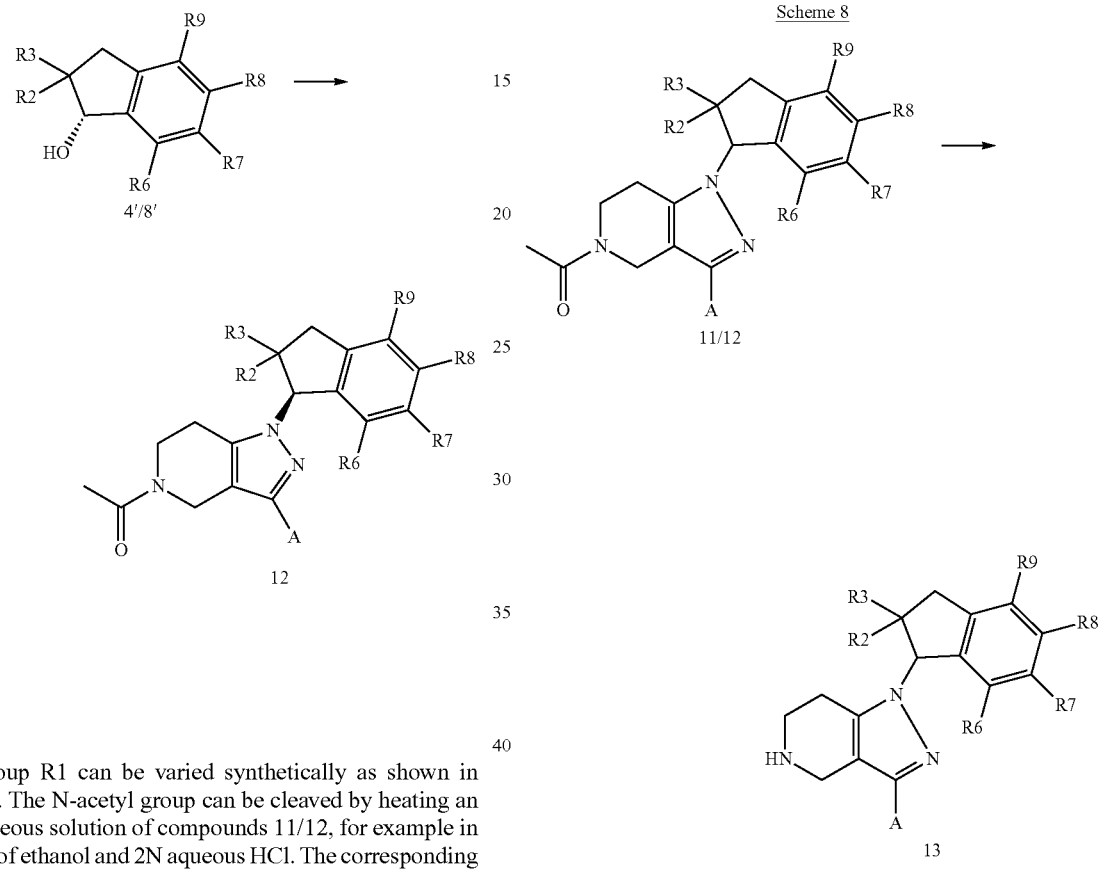

The group R1 can be varied synthetically as shown in Scheme 8. The N-acetyl group can be cleaved by heating an acidic aqueous solution of compounds 11/12, for example in a mixture of ethanol and 2N aqueous HCl. The corresponding amines 13 can be modified in a variety of ways, for example by acylation as shown in Scheme 9 in an inert solvent like CH$_2$Cl$_2$ and in the presence of a base like triethylamine. The N-acylated compounds 14 have been found to be potent TASK-1 blockers. When R2=OH sometimes diacylated compounds 15 can also be isolated as side-product which have also been found to be TASK-1 blockers. In cases where A contains a CN group (cyano group, NC—) this group can be partially converted to a carboxamide group. These side products can easily be separated.

Scheme 9

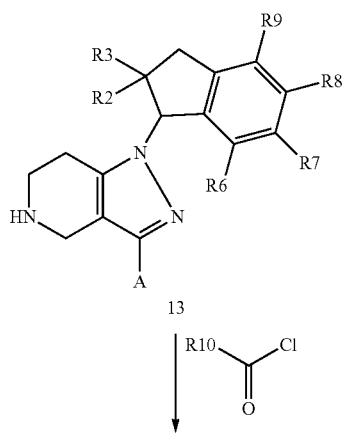

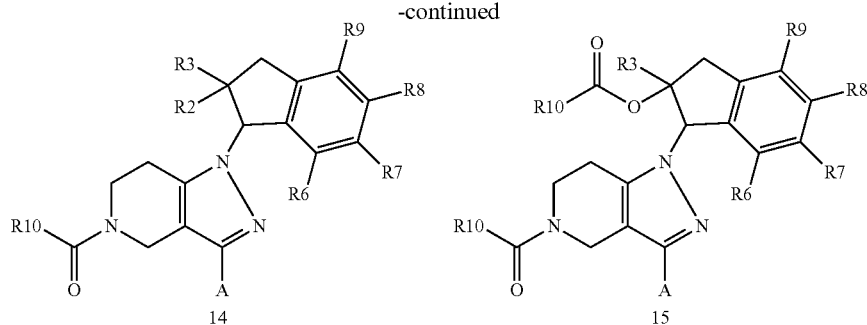

14

15

The hydroxyl group in compounds 11, wherein R3 is preferably a hydrogen can be alkylated according to Scheme 10. For example, after deprotonation with a strong base like sodium hexadimethyldisilazide or NaH and subsequent alkylation with alkyl halogenides (R-Hal, wherein R is $(C_1-C_6)$-alkyl). The alkoxy compounds 16 are obtained and have been found to be active TASK-1 blockers.

Scheme 10

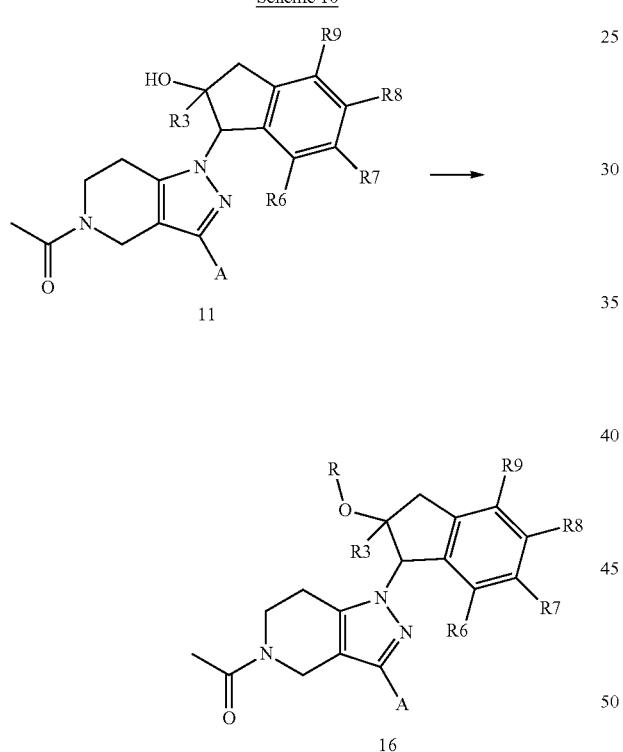

The group R1 can be varied additionally and converted to novel urethane compounds 17 as shown in Scheme 11, for example by reaction of compounds 13 with alkylchloroformates in an inert solvent like $CH_2Cl_2$ in the presence of a base like triethylamine, wherein the residue R is a $(C_1-C_6)$-alkyl group.

Scheme 11

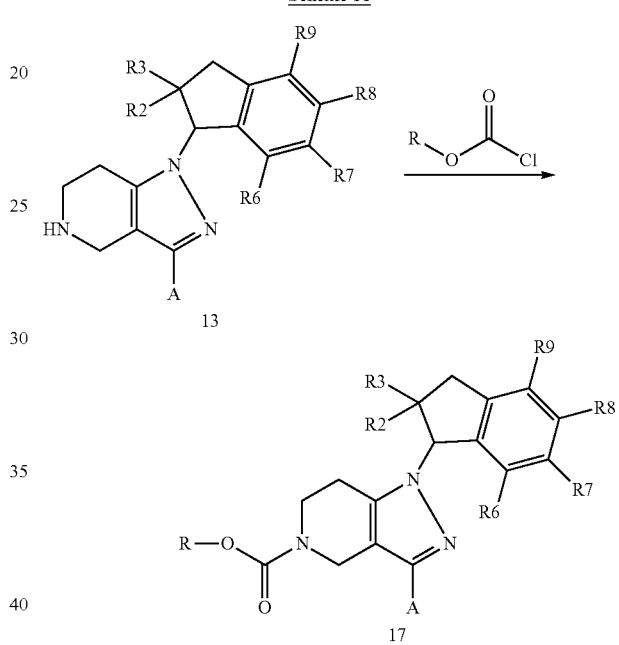

The group R1 can also be varied to novel amines 18 as shown in Scheme 12, for example by reaction of compounds 13 with unsubstituted or substituted alkyl halogenides in an inert solvent like $CH_3CN$ or DMF in the presence of a base like triethylamine. Suitable alkyl halogenides are of the formula R1-Hal, wherein R1 is selected from the residues $R^{11}$—$(C_1-C_6)$-alkyl-. Other methods can be used as reductive amination with aldehydes (for a review see E. W. Baxter and A. B. Reitz, Organic Reactions, 1, 59, 2002).

Scheme 12

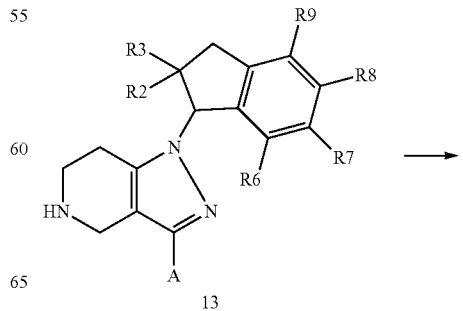

13

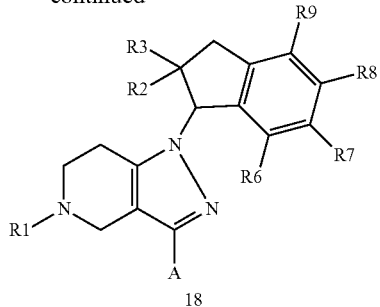

18

Alkyl groups R can be introduced in compounds starting from compounds 11'/12' where one of the groups R5, R6, R7, R8 is a halogen for example bromine according to Scheme 13. The residue R1 of compounds 11' and 12' is preferably R10-C(O)—, particular preferred CH$_3$—C(O)—. For example after treatment with tetralkyltin (SnR$_4$, wherein R is equal to a (C$_1$-C$_6$)-alkyl group) in inert solvents at high temperature in the presence of a catalyst for example tetrakis(triphenylphosphine)palladium(0) (Macdonald, Simon J. F.; McKenzie, Thomas C.; Hassen, Wesley D., Journal of the Chemical Society, Chemical Communications (1987), (20), 1528-30), novel alkyl substituted compounds 19 can be obtained which are active TASK-1 blockers.

Scheme 13

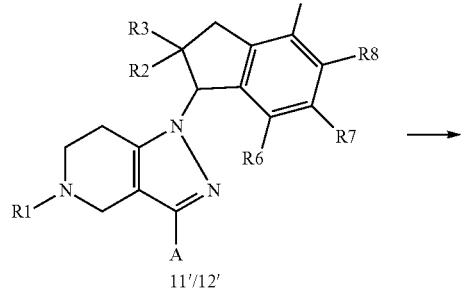

11'/12'

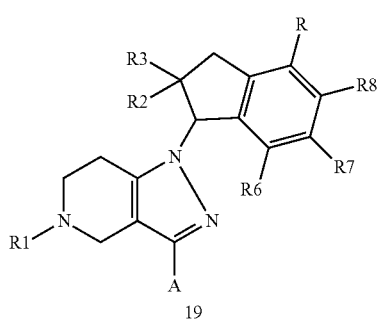

19

Cyclopropyl or aryl groups can be introduced with the Suzuki reaction (N. Miyaura, A. Suzuki: J. Chem. Soc., Chem. Commun. 1979, S. 866-867) in compounds starting from compounds 11'/12' where one of the groups R5, R6, R7, R8 is a halogen for example bromine according to Scheme 14. The residue R1 of compounds 11' and 12' is preferably R10-C(O)—, particular preferred CH$_3$—C(O)—. For example after treatment with cyclopropylboronic acid in inert solvents at high temperature in the presence of a catalyst for example tetrakis(triphenylphosphine)palladium(0) in CH$_3$CN/water with a base like K$_2$CO$_3$ novel cyclopropyl substituted compounds 20 can be obtained which are active TASK-1 blockers.

Scheme 14

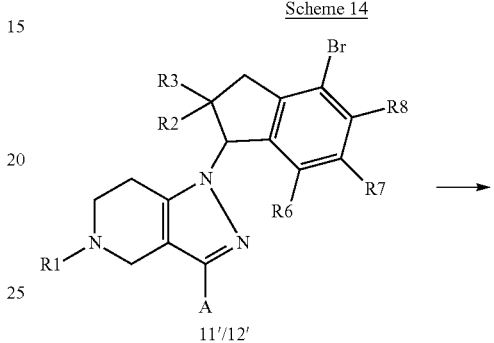

11'/12'

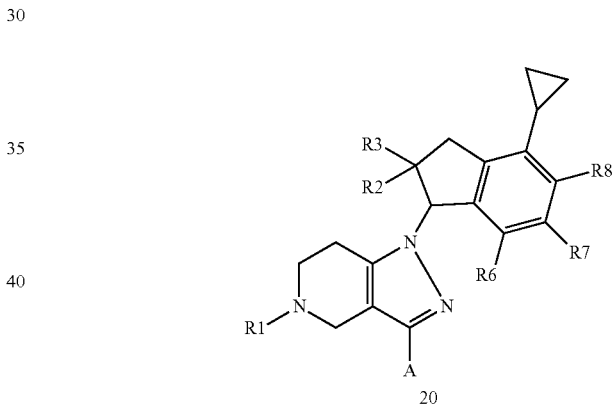

20

Halogens or nitril groups X can be introduced in compounds starting from compounds 11'/12' where one of the groups R5, R6, R7, R8 is a halogen for example bromine or iodine according to Scheme 15. The residue R1 of compounds 11' and 12' is preferably R10-C(O)—, particular preferred CH$_3$—C(O)—. For example after heating with CuX in an inter solvent for example dimethylsulfoxide at high temperature in the microwave novel X-substituted compounds 21 can be obtained which are active TASK-1 blockers. Thiol ethers 21' can sometimes be isolated additionally as by-products which come from partial decomposition of the solvent dimethylsulfoxide. These compounds can be TASK-1 blockers.

Scheme 15

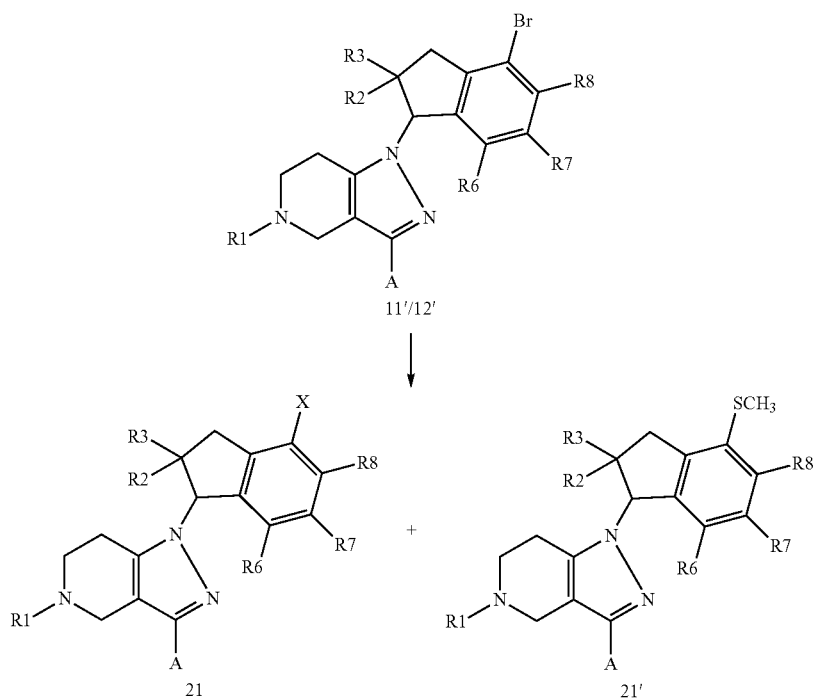

The group R1 can also be varied to novel sulfonamides 23 as shown in Scheme 16, for example by reaction of compounds 13 with alkylsulfonylchloride (R—SO$_2$Cl, wherein R is equal to a (C$_1$-C$_6$)-alkyl group) in an inert solvent like CH$_2$Cl$_2$ in the presence of a base for example triethylamine.

Scheme 16

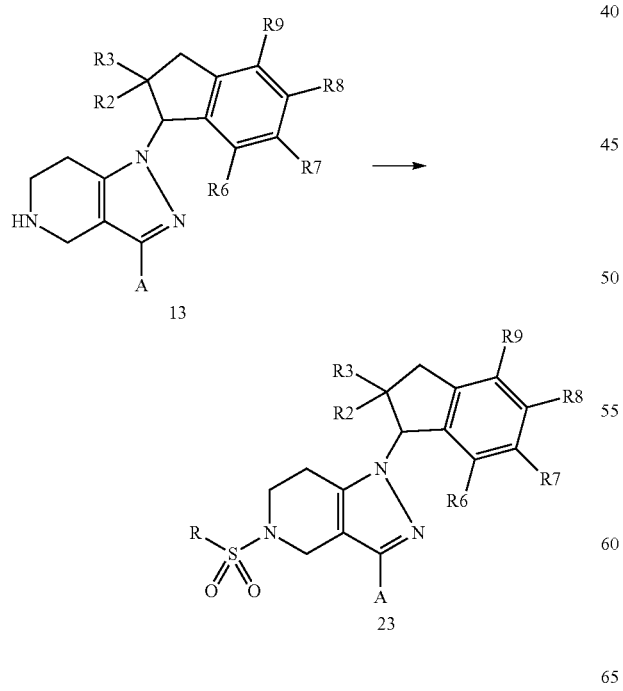

The group R1 can also be varied to novel ureas 22/22', wherein R12 in 22' is equal to a (C$_1$-C$_6$)-alkyl group, as shown in Scheme 17-18, for example by reaction of compounds 13 with isocyanates or by step-wise reaction with phosgene followed by an amine (see for example Journal of Medicinal Chemistry (2010), 53(24), 8468-8484 for a similar reaction).

Scheme 17

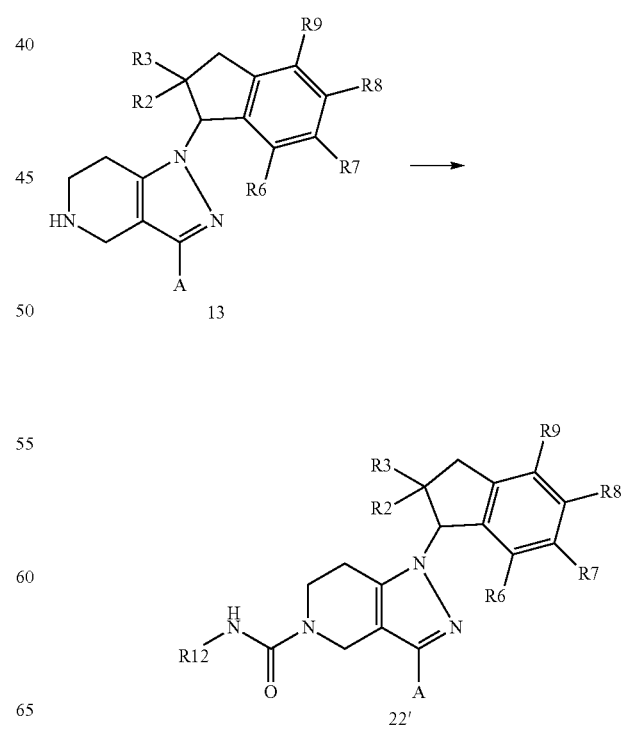

Scheme 18

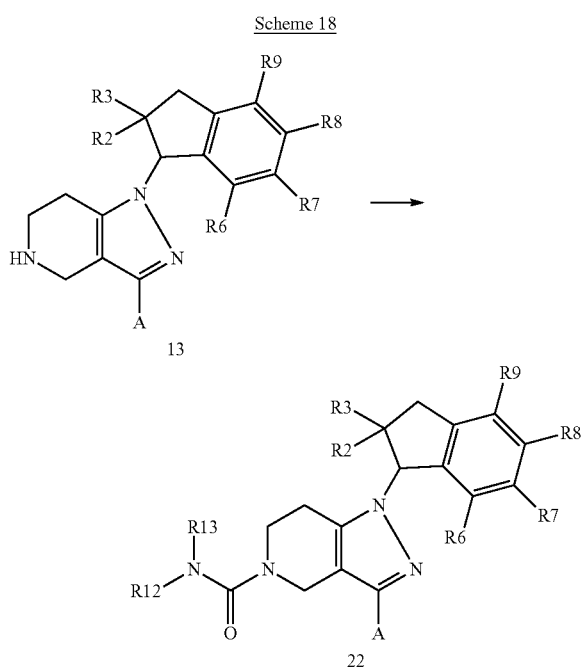

The working up and, if desired, the purification of the products and/or intermediates takes place by conventional methods such as extraction, chromatography or crystallization and conventional dryings.

For the preparation of compounds of formula I, the reactions shown in Scheme 8 to 18 can be carried out in different orders. Preferably, compounds 11/12 are prepared by a method according to Scheme 4, 5, 6 or 7. Subsequently, in compounds 11/12 a specific residue R6 to R9 according to Scheme 13, 14 or 15 may be introduced, if desired a modification of residue R2 according to Scheme 10 can be carried out, and optionally a residue R1 is introduced according to Scheme 8 and 9, 11, 12, 16, 17 or 18. Wherein, in a preferred order an introduction of a residue R6 to R9 is carried out prior to a modification of residue R2. Residue R1 is preferably introduced at last.

Owing to the TASK-1-inhibitory properties, the compounds of the formula I and/or their pharmaceutically compatible salts are suitable for the prevention and treatment of disorders which are caused by activation or by an activated TASK-1, and also of disorders in which have TASK-1-related damages appear secondary to another, primary cause.

The compounds of the formula I and/or physiologically compatible salts thereof can also be used for the treatment and prevention of disorders where TASK-1 requires only partial inhibition, for example by using a lower dosage.

The compounds of the formula I and/or their pharmaceutically acceptable salts can be employed to produce medicaments with a TASK-1 channel-blocking effect for the therapy and prophylaxis of TASK-1 channel-mediated diseases. The compounds of the formula I and/or their pharmaceutically acceptable salts can further be used for the therapy or prophylaxis of cardiac arrhythmias, e.g. of arrhythmias that respond to the changes in the shape of the action potential, mainly a prolongation of the action potential, which is induced by TASK-1 blockade.

The compounds of the formula I and/or their pharmaceutically acceptable salts can be employed for terminating existent atrial fibrillation or flutter to restore the sinus rhythm (cardioversion). In addition, the compounds reduce the susceptibility for a new development of atrial fibrillation events, thus the compounds are suitable for prophylactic treatment by maintenance of sinus rhythm (rhythm control). The substances are devoid of a ventricular proarrhythmic risk (prolongation of the QT-interval and Torsades de pointe arrhythmias).

The compounds of the formula I and/or their pharmaceutically acceptable salts can be employed for producing a medicament for the treatment and/or prevention of arrhythmias, particularly atrial trachyarrhythmias, atrial fibrillation and atrial flutter The compounds of the formula I and/or their pharmaceutically acceptable salts are further suitable for producing a medicament for the therapy or prophylaxis of sleep-related respiratory disorders, central and obstructive sleep apneas, upper airway resistance syndrome, Cheyne-Stokes respiration, snoring, disrupted central respiratory drive, sudden child death, postoperative hypoxia and apnea, muscle-related respiratory disorders, respiratory disorders after long-term mechanical ventilation (weaning), respiratory disorders during adaptation in high mountains, acute and for respiratory disorders, chronic lung disorders with hypoxia and hypercapnia, chronic obstructive pulmonary disease (COPD) and obesity hypoventilation syndrome.

The compounds of the formula I and/or their pharmaceutically acceptable salts are further suitable as a respiratory stimulant for the prevention and treatment of respiratory depression associated with anesthesia or procedural sedations for small interventions or for diagnostic purposes, for the treatment and prevention of respiratory depression by opioids in chronic pain treatment e.g. in cancer or palliative care or procedural sedations and/or for weaning from longterm mechanical ventilation.

The compounds of the formula I and/or their pharmaceutically acceptable salts are further suitable for the treatment and/or prevention of multiple sclerosis and inflammatory and degenerative disorders of the central nervous system.

The compounds of the invention of the formula I and their pharmaceutically acceptable salts can thus be used on animals, preferably on mammals, and in particular on humans, as pharmaceuticals on their own, in mixtures with one another or in the form of pharmaceutical preparations.

Thus, a further embodiment of the present invention is a pharmaceutical preparation, or a pharmaceutical composition, comprising an effective amount of a compound of the formula I and/or of its pharmaceutically acceptable salts, together with pharmaceutically acceptable carriers and additives, alone or in combination with other pharmacological active ingredients or pharmaceuticals. The pharmaceutical preparations usually comprise from 0.1 to 90 percent by weight of the compounds of the formula I and/or their pharmaceutically acceptable salts. The pharmaceutical preparations can be produced in a manner known per se. For this purpose, the compounds of the formula I and/or their pharmaceutically acceptable salts are converted together with one or more solid or liquid pharmaceutical vehicles and/or excipients and, if desired, in combination with other pharmaceutical active ingredients into a suitable dosage form, which can then be used as pharmaceutical in human medicine or veterinary medicine.

Pharmaceuticals which comprise a compound of the formula I and/or its pharmaceutically acceptable salts can moreover be administered for example orally, intravenously, intramuscular, subcutaneously, nasally, topically, pharyngeally or by inhalation, and the preferred administration depends on the individual case, for example on the particular manifestation of the disorder. The compounds of the formula I can moreover be used alone or together with pharmaceutical excipients, in particular both in veterinary and in human medicine. The pharmaceuticals comprise active ingredients of the formula I and/or their pharmaceutically acceptable salts generally in an amount of from 0.01 mg to 1 g per dose unit.

The skilled worker is familiar on the basis of his expert knowledge with which excipients are suitable for the desired pharmaceutical formulation. Besides solvents, gel formers, suppository bases, tablet excipients and other active substance carriers it is possible to use for example antioxidants, dispersants, emulsifiers, antifoams, masking flavors, preservatives, solubilizers, agents for achieving a depot effect, buffer substances or colorants.

For a form for oral use, the active compounds are mixed with the additives suitable for this purpose, such as carriers, stabilizers or inert diluents, and converted by conventional methods into suitable presentations such as tablets, coated tablets, two-piece capsules, aqueous, alcoholic or oily solutions. Examples of inert carriers which can be used are gum arabic, magnesia, magnesium carbonate, potassium phosphate, lactose, glucose or starch, especially corn starch. Preparation can take place both as dry and as wet granules. Suitable as oily carriers or as solvents are, for example, vegetable or animal oils such as sunflower oil or fish liver oil. Suitable solvents for aqueous or alcoholic solutions are, for example, water, ethanol or sugar solutions or mixtures thereof. Examples of further excipients, also for other administration forms, are polyethylene glycols and polypropylene glycols.

For subcutaneous, intramuscular or intravenous administration, the active compounds are converted if desired with the substances usual for this purpose, such as solubilizers, emulsifiers or further excipients, into a solution, suspension or emulsion. The compounds of the formula I and/or their pharmaceutically acceptable salts may also be lyophilized and the resulting lyophilizates be used, for example, for producing products for injection or infusion. Examples of suitable solvents are: water, physiological saline or alcohols, for example ethanol, propanol, glycerol, as well as sugar solutions such as glucose or mannitol solutions, or else mixtures of the various solvents mentioned.

Suitable as pharmaceutical formulation for administration in the form of aerosols or sprays are, for example, solutions, suspensions or emulsions of the active ingredient of the formula I or their pharmaceutically acceptable salts in a pharmaceutically acceptable solvent, such as in particular ethanol or water, or a mixture of such solvents. The formulation may if required also comprise other pharmaceutical excipients such as surfactants, emulsifiers and stabilizers, and a propellant gas. Such a preparation comprises the active ingredient normally in a concentration of about 0.1 to 10, in particular of about 0.3 to 3 percent by weight.

The dosage of the active ingredient to be administered or of the pharmaceutically acceptable salts thereof depends on the individual case and should be adapted to the circumstances of the individual case as usual for an optimal effect. Thus, it naturally depends on the frequency of administration and on the potency and duration of action of the particular compounds employed for therapy or prophylaxis, but also on the type and severity of the disease to be treated, and on the gender, age, weight and individual response of the human or animal to be treated, and on whether therapy is acute or prophylactic.

The daily dose of a compound of the formula I and/or its pharmaceutically acceptable salts for a patient weighing about 75 kg is normally at least 0.001 mg/kg to 100 mg/kg of body weight, preferably 0.01 mg/kg to 20 mg/kg. Even higher dosages may also be necessary for acute episodes of the disease, for example in an intensive care unit. Up to 800 mg per day may be necessary. The dose may be in the form of a single dose or be divided into a plurality, for example two, three or four, single doses. Parenteral administration by injection or infusion, for example a continuous intravenous infusion, may also be advantageous, especially in the treatment of acute cases of cardiac arrhythmias, for example in an intensive care unit.

EXAMPLES

The following examples illustrate various embodiments of the present invention.

Example 1

1-(4-Morpholin-4-yl-3,6-dihydro-2H-pyridin-1-yl)-ethanone (1)

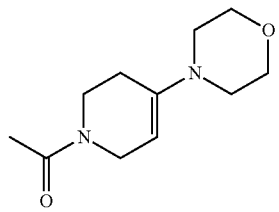

According to Scheme 1, step 1: A mixture of morpholine (67.85 g, 0.779 mol), 1-acetyl-4-piperidone (99.95 g, 0.708 mol) and para-toluenesulfonic acid monohydrate (0.366 g, 2.1 mmol) in toluene (300 ml) was heated in a Dean-Stark trap apparatus for 16 h at reflux. Solvents were evaporated in vacuo to give 149 g of 1-(4-morpholin-4-yl-3,6-dihydro-2H-pyridin-1-yl)-ethanone (1) which was used in the next step without any further purification.

Example 2 and 3

3-(5-Acetyl-4,5,6,7-tetrahydro-1H-pyrazolo[4,3-c]pyridin-3-yl)-benzonitrile (3a)

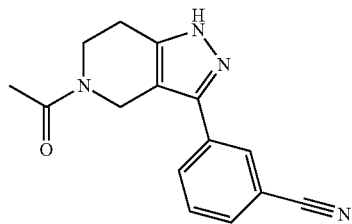 [SMILES: CC(=O)N1CCc2[nH]nc(-c3cccc(C#N)c3)c2C1]

According to Scheme 1, steps 2-3: To a solution of 1-(4-morpholin-4-yl-3,6-dihydro-2H-pyridin-1-yl)-ethanone (1) (6.35 g, 30.2 mmol) in dry dichloromethane (30 ml) at 0° C. was added triethylamine (3.056 g, 30.2 mmol) and after stirring the solution at 0° C. for 10 min, 3-cyanobenzochloride (5 g, 30.2 mmol) was added. The mixture was stirred for 45 min at 0° C. then the mixture was allowed to warm to room temperature and stirred overnight. 5% aqueous HCl was added and the mixture was stirred for 2 h. The mixture was extracted with dichloromethane and the organic layer was washed with water, filtered over a short pad of silica gel and evaporated to dryness resulting in 8 g of 3-(1-Acetyl-4-oxo-piperidine-3-carbonyl)-benzonitrile (2a) which was used immediately in the next step without purification.

To a mixture of 3-(1-Acetyl-4-oxo-piperidine-3-carbonyl)-benzonitrile (2a) (8 g, 29.6 mmol) in ethanol (26 ml) at 10° C. hydrazine hydrate (4.44 g, 88.8 mmol) was added slowly within 5 min. The mixture was stirred 3 h and allowed to warm to room temperature overnight. The mixture was concentrated to ¼ of its volume until a precipitate formed. The suspension was stirred for 2 h, cooled down and filtrated.

The solid was washed with a small amount of ethanol. A second portion of product precipitated overnight from the filtrate and was pooled with the first portion of solid to give 4.02 g of 3-(5-Acetyl-4,5,6,7-tetrahydro-1H-pyrazolo[4,3-c]pyridin-3-yl)-benzonitrile (3a) as a solid.

$R_t$=1.20 min (LC method 7). Detected mass: 267.15 [M+H$^+$]

The intermediates in the following table 1 were obtained according to Scheme 1 by following a reaction sequence according to the synthesis of (3a).

TABLE 1

| No. | Starting compound | Product | Chemical name | [M + H$^+$] | $R_t$/[min] (LC-Meth.) |
|---|---|---|---|---|---|
| 3b | 4-fluoro-benzo-chloride | | 1-[3-(4-Fluoro-phenyl)-1,4,6,7-tetrahydro-pyrazolo[4,3-c]pyridin-5-yl]-ethanone | 260.12 | 2.32 (8) |
| 3c | 6-(tri-fluoro-methyl)-pyridine-2-carbonyl-chloride | | 1-[3-(6-Tri-fluoromethyl-pyridin-2-yl)-1,4,6,7-tetrahydro-pyrazolo[4,3-c]pyridin-5-yl]-ethanone | 311.2 | 1.10 (4) |
| 3d | 3-trifluoro-methyl-benzoyl-chloride | | 1-[3-(3-Trifluoromethyl-phenyl)-1,4,6,7-tetrahydro-pyrazolo[4,3-c]pyridin-5-yl]-ethanone | 310.11 | 1.12 (4) |
| 3e | 3-trifluoro-methoxy-benzoyl-chloride | | 1-[3-(3-Trifluorometh-oxy-phenyl)-1,4,6,7-tetrahydro-pyrazolo[4,3-c]pyridin-5-yl]-ethanone | 326.16 | 3.60 (2) |
| 3f | 3-chloro-benzoyl-chloride | | 1-[3-(3-Chloro-phenyl)-1,4,6,7-tetrahydro-pyrazolo[4,3-c]pyridin-5-yl]-ethanone | 275.08 | 0.94 (4) |

TABLE 1-continued

| No. | Starting compound | Product | Chemical name | [M + H⁺] | R$_t$/[min] (LC-Meth.) |
|---|---|---|---|---|---|
| 3g | 2-fluoro-5-methoxy-benzoyl-chloride | | 1-[3-(2-Fluoro-5-methoxy-phenyl)-1,4,6,7-tetrahydro-pyrazolo[4,3-c]pyridin-5-yl]-ethanone | 290.15 | 2.97 (2) |
| 3h | 4-fluoro-3-tri-fluoro-methyl-benzoyl-chloride | | 1-[3-(4-Fluoro-3-trifluoro-methyl-phenyl)-1,4,6,7-tetrahydro-pyrazolo[4,3-c]pyridin-5-yl]-ethanone | 328.16 | 3.63 (2) |
| 3i | 3-methoxy-benzoyl-chloride | | 1-[3-(3-Methoxy-phenyl)-1,4,6,7-tetrahydro-pyrazolo[4,3-c]pyridin-5-yl]-ethanone | 272.5 | 0.99 (4) |
| 3j | 4-methyl-benzoyl-chloride | | 1-(3-p-Tolyl-1,4,6,7-tetrahydro-pyrazolo[4,3-c]pyridin-5-yl)-ethanone | 256.20 | 1.53 (9) |
| 3k | 4-fluoro-3-methoxy-benzoyl chloride | | 1-[3-(4-Fluoro-3-methoxy-phenyl)-1,4,6,7-tetrahydro-pyrazolo[4,3-c]pyridin-5-yl]-ethanone | 290.2 | 1.02 (4) |

TABLE 1-continued

| No. | Starting compound | Product | Chemical name | [M + H⁺] | $R_t$/[min] (LC-Meth.) |
|---|---|---|---|---|---|
| 3l | 4-fluoro-3-cyano-benzoyl chloride | | 5-(5-Acetyl-4,5,6,7-tetra-hydro-1H-pyrazolo[4,3-c]pyridin-3-yl)-2-fluoro-benzo-nitrile | 285.1 | 1.01 (4) |
| 3m | 4-chloro-benzoyl-chloride | | 1-[3-(4-Chloro-phenyl)-1,4,6,7-tetrahydro-pyrazolo[4,3-c]pyridin-5-yl]-ethanone | 276.17 | 1.59 (9) |
| 3n | 4-methoxy-benzoyl-chloride | | 1-[3-(4-Methoxy-phenyl)-1,4,6,7-tetrahydro-pyrazolo[4,3-c]pyridin-5-yl]-ethanone | 272.21 | 1.43 (9) |
| 3o | 3-fluoro-benzoyl-chloride | | 1-[3-(3-Fluoro-phenyl)-1,4,6,7-tetrahydro-pyrazolo[4,3-c]pyridin-5-yl]-ethanone | 260.16 | 1.47 (9) |
| 3p | 4-tri-fluoro-methyl-benzoyl-chloride | | 1-[3-(4-Tri-fluoromethyl-phenyl)-1,4,6,7-tetrahydro-pyrazolo[4,3-c]pyridin-5-yl]-ethanone | 309.9 | 1.00 (4) |

Example 4

4-Bromo-6-fluoro-indan-1-ol (4a)

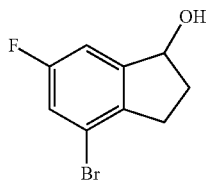 [SMILES: OC1CCc2c(Br)cc(F)cc21]

According to Scheme 2, step 1: To a solution of 4-Bromo-6-fluoro-indan-1-one (10.0 g, 43.7 mmol) in ethanol (183 ml) at 0° C. NaBH$_4$ (3.67 g, 97.0 mmol) was added in portions and then the mixture was stirred at room temperature for 18 h. After evaporation of solvents in vacuo, water was added to the residue, the solution was extracted 3 times with ethyl acetate, then 2N aqueous HCl was added and the combined organic layers were washed with saturated aq. NaHCO$_3$ and water. After drying over Na$_2$SO$_4$ and filtration, solvents were evaporated in vacuo to give 10.0 g of 4-Bromo-6-fluoro-indan-1-ol (4a) which was used immediately in the next step without purification.

R$_t$=1.19 min (LC method 4).

$^1$H-NMR (d$^6$-DMSO): δ (ppm)=1.7-1.9 (m, 1H); 2.38-2.45 (m, 1H); 2.66-2.70 (m, 1H); 2.8-2.9 (m, 1H); 5.1 (d, 1H); 5.5 (d, 1H); 7.15 (dd, 1H); 7.4 (dd, 1H).

Example 5

7-Bromo-5-fluoro-1H-indene (5a)

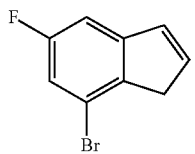

According to Scheme 2, step 2: A mixture of 4-bromo-6-fluoro-indan-1-ol (4a) (10.0 g, 43.3 mmol) and para-toluene sulfonic acid monohydrate (372 mg, 2.16 mmol) in toluene was heated at reflux for 2.5 h. The solution was washed with aqueous saturated NaHCO$_3$ and brine, dried over MgSO$_4$ and solvents evaporated to give 9.0 g of 7-Bromo-5-fluoro-1H-indene (5a) which was used immediately in the next step without purification.

R$_t$=1.38 min (LC method 4).

$^1$H-NMR (d$^6$-DMSO): δ (ppm)=2.5 (m, 2H); 3.4 (m, 2H); 6.8 (m, 1H); 7 (dt, 1H); 7.3 (m, 2H).

Example 6

1aS,6aR)-5-Bromo-3-fluoro-6,6a-dihydro-1aH-1-oxa-cyclopropa[a]indene (6a

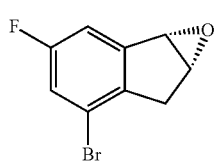

According to Scheme 2, step I/II:

Preparation of buffered sodium hypochlorite solution: To 383 ml water 67.5 ml commercial NaOCl solution (10-13% free chlorine) were added and the pH was adjusted to 11.3 by addition of small amounts of NaH$_2$PO$_4$. The solution was stored at 4° C. for maximum 24 h.

To a solution of 9 g (42.3 mmol) of 7-Bromo-5-fluoro-1H-indene (5a) in CH$_2$Cl$_2$ at 0° C. was added (S,S)-(+)-N,N'-bis(3,5-di-tert-butylsalicylidene)-1,2-cyclohexanediaminomanganese(III)-chloride (Jacobsen catalyst; 1.2 g, 1.7 mmol) and 4-(3-phenylpropyl)pyridine N-oxide (1.8 g, 8.5 mmol). After stirring for 15 min at 0° C., the 0° C. cold buffered sodium hypochlorite solution was added and the mixture was stirred at 0° C. for 3 h. The resulting liquid layers were separated and the aqueous layer was extracted 3 times with CH$_2$Cl$_2$. The combined organic layers were washed with brine and dried over MgSO$_4$. Solvents were evaporated and the crude product was purified by silica gel chromatography (eluting with 5 to 50% ethyl acetate in heptane). The product was recrystallized from heptane to give 3.2 g of (1aS,6aR)-5-Bromo-3-fluoro-6,6a-dihydro-1aH-1-oxa-cyclopropa[a]indene (6a) as white needles.

R$_t$=1.25 min (LC method 4).

$^1$H-NMR (d$^6$-DMSO): δ (ppm)=2.9 (m, 1H); 3.0 (m, 1H); 4.26 (t, 1H); 4.47 (dd, 1H); 7.4 (dd 1H); 7.5 (dd, 1H).

The intermediates in the following table 2 were obtained according to Scheme 2 by following the reaction sequence as used for synthesis of (6a).

TABLE 2

| No. | Starting compound | Product | Chemical Name | R$_t$/[min] (LC-Meth.) |
|---|---|---|---|---|
| 6b | 4,6-difluoro-indan-1-one | 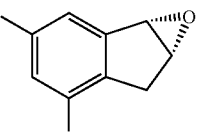 | (1aS,6aR)-3,5-Difluoro-6,6a-dihydro-1aH-1-oxa-cyclopropa[a]indene | 3.91 (2) |
| 6c | 4,6-dichloro-indan-1-one | 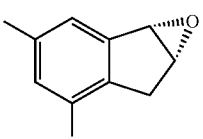 | (1aS,6aR)-3,5-Dichloro-6,6a-dihydro-1aH-1-oxa-cyclopropa[a]indene | 1.96 (9) |

TABLE 2-continued

| No. | Starting compound | Product | Chemical Name | $R_t$/[min] (LC-Meth.) |
|---|---|---|---|---|
| 6d | 6-chloro-4-fluoro-indan-1-ol | | (1aS,6aR)-3-Chloro-5-fluoro-6,6a-dihydro-1aH-1-oxa-cyclopropa[a]indene | 1.84 (9) |
| 6e | 6-chloro-indan-1-ol | | (1aS,6aR)-3-Chloro-6,6a-dihydro-1aH-1-oxa-cyclopropa[a]indeneNo. | 1.76 (9) |

The compounds were characterized by $^1$H-NMR spectroscopy as follows:

| No. | $^1$H-NMR (d$^6$-DMSO) |
|---|---|
| 6b | δ (ppm) = 2.9 (d, 1H); 3.1 (d, 1H); 4.26 (t, 1H); 4.44 (m 1H); 7.33-7.35 (1H, dt); 7.11-7.16 (1H, dd) |
| 6c | δ (ppm) = 2.93-2.98 (d, 1H); 3.06-3.10 (d, 1H); 4.25 (t, 1H); 4.46 (m, 1H); 7.55 (d, 1H); 7.69 (d, 1H) |
| 6d | δ (ppm) = 2.95-2.99 (d, 1H); 3.11-3.15 (d, 1H); 4.24 (t, 1H); 4.40 (m, 1H); 7.34 (dd, 1H); 7.50 (d, 1H) |
| 6e | δ (ppm) = 2.92-2.97(dd, 1H); 3.05-3.09 (d, 1H); 4.18 (t, 1H); 4.36 (d, 1H); 7.26-7.32 (m 2H); 7.62 (d, 1H) |

The intermediate in the following table 3 was obtained according to Scheme 2 by following a reaction sequence according to the synthesis of (6a), but using (R,R-(+)-N,N'-bis(3,5-di-tert-butylsalicylidene)-1,2-cyclohexanediaminomanganese(III) chloride (Jacobsen catalyst) in the last step.

TABLE 3

| No. | Starting compound | Product | Chemical name | $R_t$/[min] (LC-Meth.) |
|---|---|---|---|---|
| 6f | 5,7-difluoro-1H-indene | | (1aR,6aS)-3,5-Difluoro-6,6a-dihydro-1aH-1-oxa-cyclopropa[a]indene | 1.04 (4) |

The compound was characterized by $^1$H-NMR spectroscopy as follows:

| No. | $^1$H-NMR (d$^6$-DMSO) |
|---|---|
| 6f | δ (ppm) = 2.93-2.97 (d, 1H); 3.09-3.13 (d, 1H); 4.24 (t, 1H); 4.42 (m, 1H); 7.12-7.15 (dt 1H); 7.34 (dd, 1H) |

Racemic(1aS,6aR)-3,4-Dichloro-6,6a-dihydro-1aH-1-oxa-cyclopropa[a]indene (6g)

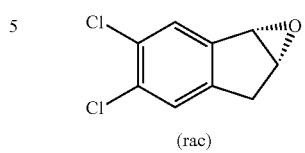

(rac)

According to Scheme 2, step IV: To a solution of 5,6-dichloro-1H-indene (5f) (1.28 g, 6.92 mmol), which was obtained according to Scheme 2 by following a reaction sequence according to synthesis of (5a), in dimethylsulfoxide (6.5 ml) and water (0.16 ml) N-bromosuccinimide (2.44 g, 13.7 mmol) was added at 10° C. and the mixture was stirred at 25° C. for 1 h. The mixture was poured on water, stirred for 30 min and the solid material was filtered off. The crude product was purified by silica gel chromatography (eluting with 0 to 50% ethyl acetate in heptane) to give 1.46 g of 2-bromo-5,6-dichloro-indan-1-ol which was immediately dissolved in tetrahydrofuran (35 ml). Finely powdered NaOH (1.37 g, 34.2 mmol) was added and the mixture was stirred at 25° C. for 2 h. The mixture was filtered through a short pad of celite and washed with a small amount of ethyl acetate. The filtrate was evaporated to dryness to give 1 g of racemic(1aS,6aR)-3,4-Dichloro-6,6a-dihydro-1aH-1-oxa-cyclopropa[a]indene (6f), which was used in the next step without purification.

$R_t$=1.90 min (LC method 9).
$^1$H-NMR (d$^6$-DMSO): δ (ppm)=2.96-2.99 (dd, 1H); 3.07-3.11 (d, 1H); 4.20 (t, 1H); 4.38 (d, 1H); 7.54 (s, 1H); 7.83 (s, 1H).

Racemic(1aS,6aR)-2,4-Dichloro-6,6a-dihydro-1aH-1-oxa-cyclopropa[a]indene (6h)

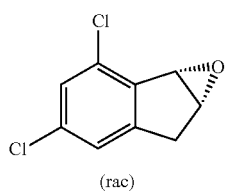 [SMILES: Clc1cc(Cl)c2c(c1)C[C@H]1O[C@@H]21]

(rac)

According to Scheme 2, step III: To a solution of 5,6-dichloro-1H-indene (5g) (4.35 g, 23.5 mmol), which was obtained according to Scheme 2 by following a reaction sequence according to synthesis of (5a), in CH$_2$Cl$_2$ (80 ml) was added meta-chloroperbenzoic acid (6.28 g, 25.5 mmol) and the mixture was stirred at 25° C. for 16 h. The mixture was diluted with CH$_2$Cl$_2$, the solid filtered off. The solution was washed with aqueous saturated Na$_2$S$_2$O$_3$ solution, with aqueous saturated NaHCO$_3$ and water, dried over Na$_2$SO$_4$, filtrated and the solution was evaporated to dryness. The crude product was purified by silica gel chromatography (eluting with 15 to 100% ethyl acetate in heptane to give 2.84 g of racemic(1aS,6aR)-2,4-Dichloro-6,6a-dihydro-1aH-1-oxa-cyclopropa[a]indene (6g).

$R_t$=2.22 min (LC method 9).
$^1$H-NMR (d$^6$-DMSO): δ (ppm)=3.06-3.1 (dd, 1H); 3.17-3.20 (d, 1H); 4.21 (t, 1H); 4.47 (d, 1H); 7.35 (s, 1H); 7.43 (s, 1H).

Example 7

4,6-Difluoro-2-methyl-indan-1-one (7a)

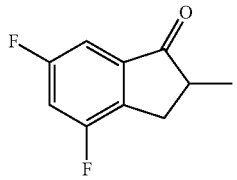

According to Scheme 3, step 1: to a solution of 4,6-difluoro-indan-1-one (5.0 g, 29.8 mmol) in dry tetrahydrofuran (100 ml) at −78° C. a 2M solution of lithiumdiisopropylamide (16.4 ml, 32.7 mmol) in tetrahydrofuran was added dropwise and the mixture was stirred for 1 h at −78° C. Then iodomethane (4.64 g, 32.7 mmol) was added and the mixture was slowly warmed to 25° C. After addition of aqueous saturated NaHCO$_3$ the mixture was extracted 3 times with ethyl acetate. The combined organic layers were dried over Na$_2$SO$_4$ and filtered, solvents were evaporated in vacuo. The crude product was purified by silica gel chromatography (eluting with 0% to 100% ethyl acetate in heptane to give 1.15 g of 4,6-Difluoro-2-methyl-indan-1-one (7a).

$R_t$=4.28 min (LC method 2). Detected mass: 183.25 [M+H$^+$]

Example 8

4,6-Difluoro-2-methyl-indan-1-ol (8a)

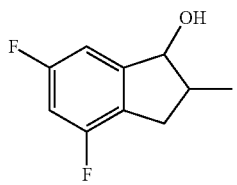

According to Scheme 3, step 2: to a solution 4,6-Difluoro-2-methyl-indan-1-one (7a) (1.27 g, 6.97 mmol) in ethanol (30 ml) NaBH$_4$ (0.26 g, 6.97 mmol) was added in portions at 0° C. and then the mixture was stirred at room temperature for 18 h. After evaporation of solvents in vacuo, water was added to the residue, the solution was extracted 3 times with ethyl acetate, then 2N aqueous HCl was added and the combined organic layers were washed with saturated aq. NaHCO$_3$ and water. After drying over Na$_2$SO$_4$ and filtration, solvents were evaporated in vacuo to give 650 mg 4,6-Difluoro-2-methyl-indan-1-ol (8a) which was used immediately in the next step without purification.

$R_t$=3.97 min (LC method 2).

$^1$H-NMR (d$^6$-DMSO): δ (ppm)=0.96 (d, 3H); 1.2 (3H, d); 2.1-2.6 (m, 2H); 2.84-2.89 (m, 0.4H); 2.98-3.03 (m, 0.6H); 4.5 (m, 0.6H); 4.85 (m, 0.4H); 5.24 (d; 0.4H); 5.59 (d, 0.6H); 6.93-7.02 (m, 2H).

Example 9

5,7-Difluoro-2-methyl-1H-indene (9a)

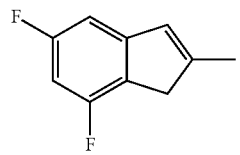

According to Scheme 3, step 3: A mixture of 4,6-Difluoro-2-methyl-indan-1-ol (8a) (0.65 g, 3.53 mmol) and para-toluene sulfonic acid monohydrate (30 mg, 0.18 mmol) in toluene was heated at reflux for 1 h. The solution was washed with aqueous saturated NaHCO$_3$ and brine, dried over MgSO$_4$ and solvents evaporated. The crude product was purified by silica gel chromatography (eluting with 0% to 100% ethyl acetate in heptane to give 0.50 g of 5,7-Difluoro-2-methyl-1H-indene (9a) which was used immediately in the next step.

$R_t$=4.90 min (LC method 2).

$^1$H-NMR (d$^6$-DMSO): δ (ppm) 2.15, (s, 3H); 2.50 (m, 2H); 6.54 (m, 1H); 6.83-6.88 (dt, 1H); 6.98-7.00 (dd, 1H).

Example 10

Racemic(1aS,6aR)-3,5-Difluoro-6a-methyl-6,6a-dihydro-1aH-1-oxa-cyclopropa[a]indene (10a)

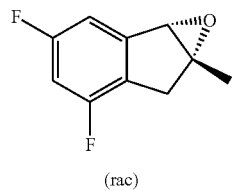

According to Scheme 2, step 4: To a solution of 5,7-Difluoro-2-methyl-1H-indene (9a) (0.44 g, 2.65 mmol) in CH$_2$Cl$_2$ (3 ml) meta-chloroperbenzoic acid (707 mg, 2.87 mmol) was added and the mixture was stirred at 25° C. for 16 h. The mixture was diluted with CH$_2$Cl$_2$ and the solid filtered off. The solution was washed with aqueous saturated Na$_2$S$_2$O$_3$ solution, with aqueous saturated NaHCO$_3$ and water, dried over Na$_2$SO$_4$, filtrated and the solution was evaporated to dryness to give 242 mg of racemic(1aS,6aR)-3,5-Difluoro-6a-methyl-6,6a-dihydro-1aH-1-oxa-cyclopropa[a]indene (10a).

$R_t$=1.81 min (LC method 9).

$^1$H-NMR (d$^6$-DMSO): δ (ppm)=1.62 (s, 3H); 2.89-2.93 (d, 1H); 3.05-3.08 (d, 1H); 4.22 (s, 1H); 7.09-7.13 (dt, 1H); 7.28-7.30 (dd, 1H).

Example 11

1-[1-((1R,2R)-4,6-Difluoro-2-hydroxy-indan-1-yl)-3-(3-trifluoromethoxy-phenyl)-1,4,6,7-tetrahydro-pyrazolo[4,3-c]pyridin-5-yl]-ethanone (11a)

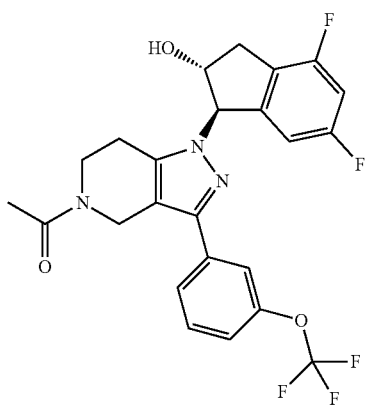 [SMILES: CC(=O)N1CCc2c(c(-c3cccc(OC(F)(F)F)c3)nn2[C@@H]2c3cc(F)cc(F)c3C[C@H]2O)C1]

According to Scheme 4:

A mixture of 1-[3-(3-trifluoromethoxy-phenyl)-1,4,6,7-tetrahydro-pyrazolo[4,3-c]pyridin-5-yl]-ethanone (3e) (0.461 mmol), 0.44 g, 2.65 mmol), (1aS,6aR)-3,5-difluoro-6,6a-dihydro-1aH-1-oxa-cyclopropa[a]indene (6b) (0.077 g, 0.461 mmol) and $K_2CO_3$ (127 mg, 0.922 mmol) in 5 ml $CH_3CN$ was stirred at 50° C. for 24 h. Water was added, the mixture was extracted 3 times with $CH_2Cl_2$, the combined organic layers were dried over $MgSO_4$, filtrated and the solution was evaporated to dryness. The crude product was purified by reverse phase HPLC ($CH_3CN$/water gradient with 0.1% trifluoroacetic acid) to give 53 mg of 1-[1-((1R,2R)-4,6-difluoro-2-hydroxy-indan-1-yl)-3-(3-trifluoromethoxy-phenyl)-1,4,6,7-tetrahydro-pyrazolo[4,3-c]pyridin-5-yl]-ethanone (11a).

$R_t$=1.2 min (LC method 4). Detected mass: 494.14 [M+H$^+$]

The example compounds in the following table 4 were obtained according to Schemes 4-6 by following a reaction according to the synthesis of (11a). Reaction conditions varied slightly by reaction time (1-3 days), temperature (50-80° C.) and 1-3 equivalents of the epoxide.

TABLE 4

| Comp. No. | Product (starting compounds) | Chemical Name | [M + H$^+$] | $R_t$/[min] (LC-Meth.) |
|---|---|---|---|---|
| 11b | (3f + 6f) | 1-[3-(3-Chloro-phenyl)-1-((1S,2S)-4,6-difluoro-2-hydroxy-indan-1-yl)-1,4,6,7-tetrahydro-pyrazolo[4,3-c]pyridin-5-yl]-ethanone | 444.21 | 1.15 (1) |
| 11c | (3g + 6b) | 1-[1-((1R,2R)-4,6-Difluoro-2-hydroxy-indan-1-yl)-3-(2-fluoro-5-methoxy-phenyl)-1,4,6,7-tetrahydro-pyrazolo[4,3-c]pyridin-5-yl]-ethanone | 458.16 | 1.1 (4) |

TABLE 4-continued

| Comp. No. | Product (starting compounds) | Chemical Name | [M + H⁺] | R$_t$/[min] (LC-Meth.) |
|---|---|---|---|---|
| 11d | (3a + 6a) | 3-[5-Acetyl-1-((1R,2R)-4-bromo-6-fluoro-2-hydroxy-indan-1-yl)-4,5,6,7-tetrahydro-1H-pyrazolo[4,3-c]pyridin-3-yl]-benzonitrile | 495.06 | 1.24 (4) |
| 11e | (3c + 6b) | 1-[1-((1R,2R)-4,6-Difluoro-2-hydroxy-indan-1-yl)-3-(6-trifluoromethyl-pyridin-2-yl)-1,4,6,7-tetrahydro-pyrazolo[4,3-c]pyridin-5-yl]-ethanone | 479.18 | 1.27 (4) |
| 11f | (3c + 6b) | 1-[1-((1R,2R)-4,6-Difluoro-2-hydroxy-indan-1-yl)-3-(4-fluoro-3-trifluoromethyl-phenyl)-1,4,6,7-tetrahydro-pyrazolo[4,3-c]pyridin-5-yl]-ethanone | 496.18 | 1.18 (1) |
| 11g | (3a + 6c) | 3-[5-Acetyl-1-((1R,2R)-4,6-dichloro-2-hydroxy-indan-1-yl)-4,5,6,7-tetrahydro-1H-pyrazolo[4,3-c]pyridin-3-yl]-benzonitrile | 467.02 | 1.28 (4) |

TABLE 4-continued

| Comp. No. | Product (starting compounds) | Chemical Name | [M + H+] | R₁/[min] (LC-Meth.) |
|---|---|---|---|---|
| 11h | (3d + 6f) | 1-[1-((1S,2S)-4,6-Difluoro-2-hydroxy-indan-1-yl)-3-(3-trifluoromethyl-phenyl)-1,4,6,7-tetrahydro-pyrazolo[4,3-c]pyridin-5-yl]-ethanone | 478.22 | 1.17 (1) |
| 11i | (rac) (3h + 10a) | racemic 1-[1-((1S,2S)-4,6-Difluoro-2-hydroxy-2-methyl-indan-1-yl)-3-(4-fluoro-3-trifluoromethyl-phenyl)-1,4,6,7-tetrahydro-pyrazolo[4,3-c]pyridin-5-yl]-ethanone | 510.21 | 1.32 (4) |
| 11j | (3a + 6d) | 3-[5-Acetyl-1-((1R,2R)-6-chloro-4-fluoro-2-hydroxy-indan-1-yl)-4,5,6,7-tetrahydro-1H-pyrazolo[4,3-c]pyridin-3-yl]-benzonitrile | 451.17 | 1.12 (1) |
| 11k | (3i + 6a) | 1-[1-((1R,2R)-4,6-Difluoro-2-hydroxy-indan-1-yl)-3-(3-methoxy-phenyl)-1,4,6,7-tetrahydro-pyrazolo[4,3-c]pyridin-5-yl]-ethanone | 440.23 | 1.23 (4) |

TABLE 4-continued

| Comp. No. | Product (starting compounds) | Chemical Name | [M + H⁺] | R_t/[min] (LC-Meth.) |
|---|---|---|---|---|
| 11l | 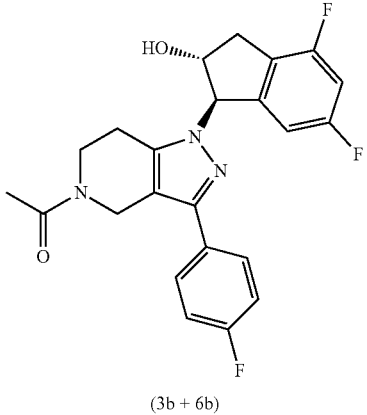 [SMILES: CC(=O)N1CCc2c(c(-c3ccc(F)cc3)nn2[C@@H]2c3cc(F)cc(F)c3C[C@H]2O)C1] (3b + 6b) | 1-[1-((1R,2R)-4,6-Difluoro-2-hydroxy-indan-1-yl)-3-(4-fluorophenyl)-1,4,6,7-tetrahydro-pyrazolo[4,3-c]pyridin-5-yl]-ethanone | 428.18 | 1.1 (1) |
| 11m | 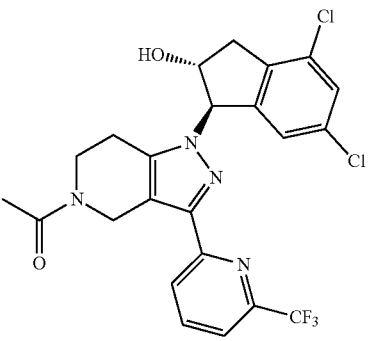 (3c + 6c) | 1-[1-((1R,2R)-4,6-Dichloro-2-hydroxy-indan-1-yl)-3-(6-trifluoromethyl-pyridin-2-yl)-1,4,6,7-tetrahydro-pyrazolo[4,3-c]pyridin-5-yl]-ethanone | 511.17 | 1.35 (4) |
| 11n | 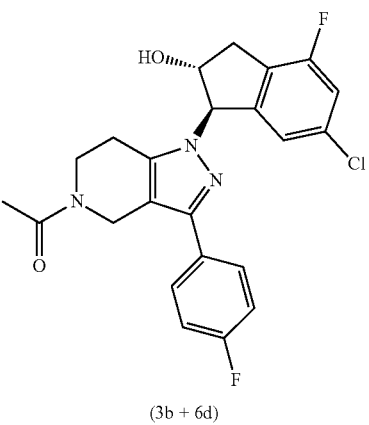 [SMILES: CC(=O)N1CCc2c(c(-c3ccc(F)cc3)nn2[C@@H]2c3cc(Cl)cc(F)c3C[C@H]2O)C1] (3b + 6d) | 1-[1-((1R,2R)-6-Chloro-4-fluoro-2-hydroxy-indan-1-yl)-3-(4-fluorophenyl)-1,4,6,7-tetrahydro-pyrazolo[4,3-c]pyridin-5-yl]-ethanone | 444.17 | 2.35 (5) |

TABLE 4-continued

| Comp. No. | Product (starting compounds) | Chemical Name | [M + H⁺] | R_t[min] (LC-Meth.) |
|---|---|---|---|---|
| 11o | (3a + 6f) | 3-[5-Acetyl-1-((1S,2S)-4,6-difluoro-2-hydroxy-indan-1-yl)-4,5,6,7-tetrahydro-1H-pyrazolo[4,3-c]pyridin-3-yl]-benzonitrile | 435.18 | 1.21 (4) |
| 11p | (3a + 6e) | 3-[5-Acetyl-1-((1R,2R)-6-chloro-2-hydroxy-indan-1-yl)-4,5,6,7-tetrahydro-1H-pyrazolo[4,3-c]pyridin-3-yl]-benzonitrile | 433.19 | 1.22 (4) |
| 11q | (3d + 6b) | 1-[1-((1R,2R)-4,6-Difluoro-2-hydroxy-indan-1-yl)-3-(3-trifluoromethyl-phenyl)-1,4,6,7-tetrahydro-pyrazolo[4,3-c]pyridin-5-yl]-ethanone | 478.19 | 1.3 (4) |
| 11r | (3e + 6f) | 1-[1-((1S,2S)-4,6-Difluoro-2-hydroxy-indan-1-yl)-3-(3-trifluoromethoxy-phenyl)-1,4,6,7-tetrahydro-pyrazolo[4,3-c]pyridin-5-yl]-ethanone | 494.19 | 1.32 (4) |

TABLE 4-continued

| Comp. No. | Product (starting compounds) | Chemical Name | [M + H+] | R_t/[min] (LC-Meth.) |
|---|---|---|---|---|
| 11s | (3b + 6e) | 1-[1-((1R,2R)-6-Chloro-2-hydroxy-indan-1-yl)-3-(4-fluoro-phenyl)-1,4,6,7-tetrahydro-pyrazolo[4,3-c]pyridin-5-yl]-ethanone | 426.11 | 2.27 (3) |
| 11t | (3a + 6b) | 3-[5-Acetyl-1-((1R,2R)-4,6-difluoro-2-hydroxy-indan-1-yl)-4,5,6,7-tetrahydro-1H-pyrazolo[4,3-c]pyridin-3-yl]-benzonitrile | 435.26 | 4.08 (2) |
| 11u | (rac) (3b + 6g) | racemic 1-[1-((1R,2R)-5,6-Dichloro-2-hydroxy-indan-1-yl)-3-(4-fluoro-phenyl)-1,4,6,7-tetrahydro-pyrazolo[4,3-c]pyridin-5-yl]-ethanone | 460.18 | 2.4 (5) |
| 11v | (3f + 6b) | 1-[3-(3-Chloro-phenyl)-1-((1R,2R)-4,6-difluoro-2-hydroxy-indan-1-yl)-1,4,6,7-tetrahydro-pyrazolo[4,3-c]pyridin-5-yl]-ethanone | 444.23 | 1.28 (4) |

TABLE 4-continued

| Comp. No. | Product (starting compounds) | Chemical Name | [M + H⁺] | R_t[min] (LC-Meth.) |
|---|---|---|---|---|
| 11w | (rac) (3a + 10a) | Racemic 3-[5-Acetyl-1-((1R,2R)-4,6-difluoro-2-hydroxy-2-methyl-indan-1-yl)-4,5,6,7-tetrahydro-1H-pyrazolo[4,3-c]pyridin-3-yl]-benzonitrile | 449.16 | 1.21 (4) |
| 11x | (3j + 6b) | 1-[1-((1R,2R)-4,6-Difluoro-2-hydroxy-indan-1-yl)-3-p-tolyl-1,4,6,7-tetrahydro-pyrazolo[4,3-c]pyridin-5-yl]-ethanone | 424.28 | 1.26 (4) |
| 11y | (3k + 6b) | 1-[1-((1R,2R)-4,6-Difluoro-2-hydroxy-indan-1-yl)-3-(4-fluoro-3-methoxy-phenyl)-1,4,6,7-tetrahydro-pyrazolo[4,3-c]pyridin-5-yl]-ethanone | 458.33 | 1.1 (1) |

TABLE 4-continued

| Comp. No. | Product (starting compounds) | Chemical Name | [M + H⁺] | $R_t$/[min] (LC-Meth.) |
|---|---|---|---|---|
| 11z | 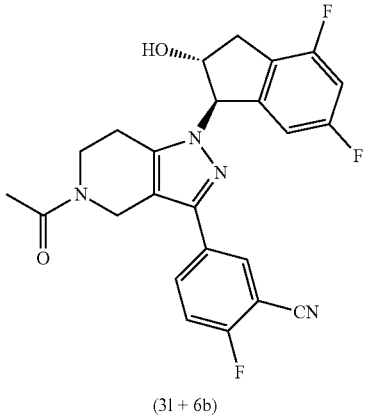 [SMILES: CC(=O)N1CCc2c(c(-c3ccc(F)c(C#N)c3)nn2[C@@H]2c3cc(F)cc(F)c3C[C@H]2O)C1] (3l + 6b) | 5-[5-Acetyl-1-((1R,2R)-4,6-difluoro-2-hydroxy-indan-1-yl)-4,5,6,7-tetrahydro-1H-pyrazolo[4,3-c]pyridin-3-yl]-2-fluoro-benzonitrile | 453.28 | 1.1 (1) |
| 11aa | 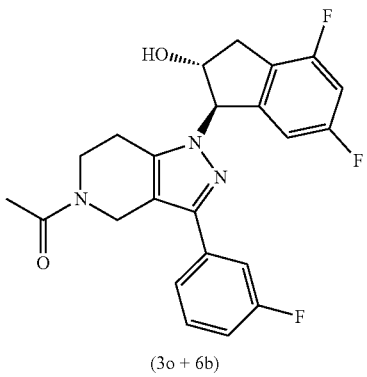 [SMILES: CC(=O)N1CCc2c(c(-c3cccc(F)c3)nn2[C@@H]2c3cc(F)cc(F)c3C[C@H]2O)C1] (3o + 6b) | 1-[1-((1R,2R)-4,6-Difluoro-2-hydroxy-indan-1-yl)-3-(3-fluoro-phenyl)-1,4,6,7-tetrahydro-pyrazolo[4,3-c]pyridin-5-yl]-ethanone | 428.21 | 1.25 (4) |
| 11ab | 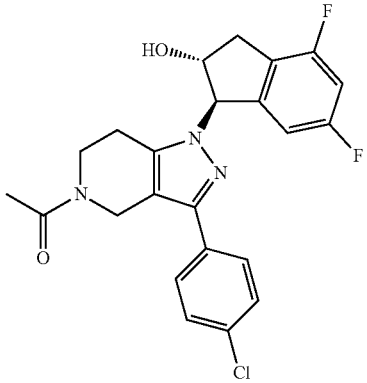 (3m + 6b) | 1-[3-(4-Chloro-phenyl)-1-((1R,2R)-4,6-difluoro-2-hydroxy-indan-1-yl)-1,4,6,7-tetrahydro-pyrazolo[4,3-c]pyridin-5-yl]-ethanone | 444.23 | 1.29 (4) |

TABLE 4-continued

| Comp. No. | Product (starting compounds) | Chemical Name | [M + H⁺] | $R_t$/[min] (LC-Meth.) |
|---|---|---|---|---|
| 11ac | 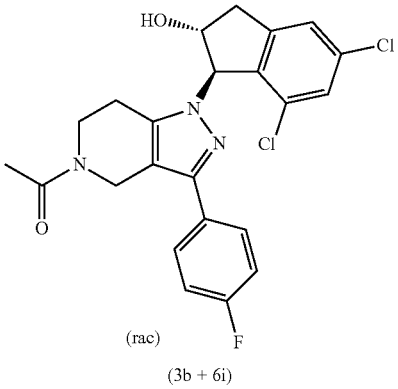 [SMILES: CC(=O)N1CCc2c(c(-c3ccc(F)cc3)nn2[C@@H]2c3c(Cl)cc(Cl)cc3C[C@H]2O)C1] (rac) (3b + 6i) | racemic 1-[1-((1R,2R)-5,7-Dichloro-2-hydroxy-indan-1-yl)-3-(4-fluoro-phenyl)-1,4,6,7-tetrahydro-pyrazolo[4,3-c]pyridin-5-yl]-ethanone | 460.17 | 2.37 (5) |
| 11ad | 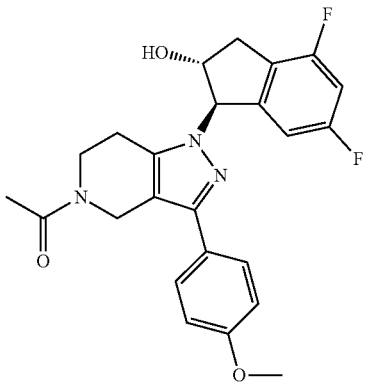 (3n + 6b) | 1-[1-((1R,2R)-4,6-Difluoro-2-hydroxy-indan-1-yl)-3-(4-methoxy-phenyl)-1,4,6,7-tetrahydro-pyrazolo[4,3-c]pyridin-5-yl]-ethanone | 440.25 | 1.22 (4) |
| 11ae | 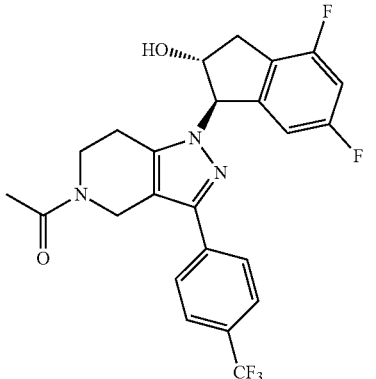 (3p + 6b) | 1-[1-((1R,2R)-4,6-Difluoro-2-hydroxy-indan-1-yl)-3-(4-trifluoromethyl-phenyl)-1,4,6,7-tetrahydro-pyrazolo[4,3-c]pyridin-5-yl]-ethanone | 478.26 | 1.17 (1) |

Example 12

1-[(R)-3-(4-Fluoro-phenyl)-1-indan-1-yl-1,4,6,7-tetrahydro-pyrazolo[4,3-c]pyridin-5-yl]-ethanone (12a)

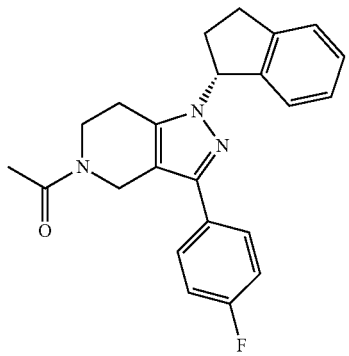 [SMILES: CC(=O)N1CCc2c(c(-c3ccc(F)cc3)nn2[C@@H]2CCc3ccccc32)C1]

According to Scheme 7: A mixture of 1-[3-(4-fluoro-phenyl)-1,4,6,7-tetrahydro-pyrazolo[4,3-c]pyridin-5-yl]-ethanone (3b) (0.2 g, 0.771 mmol), tri-n-butylphosphine (0.312 g, 1.54 mmol), 1,1'-(azodicarbonyl)dipiperidine (0.389 g, 1.54 mmol) and (S)-1-indanol in dry toluene (2.5 ml) was stirred at 80° C. for 2 h. Solvents were evaporated in vacuo. The crude product was purified by reverse phase HPLC (CH$_3$CN/water gradient with 0.1% trifluoroacetic acid) to give 81 mg of 1-[(R)-3-(4-fluoro-phenyl)-1-indan-1-yl-1,4,6,7-tetrahydro-pyrazolo[4,3-c]pyridin-5-yl]-ethanone (12a)

R$_t$=2.46 min (LC method 6). Detected mass: 376.17 [M+H$^+$].

1-[(S)-3-(4-Fluoro-phenyl)-1-indan-1-yl-1,4,6,7-tetrahydro-pyrazolo[4,3-c]pyridin-5-yl]-ethanone (12b)

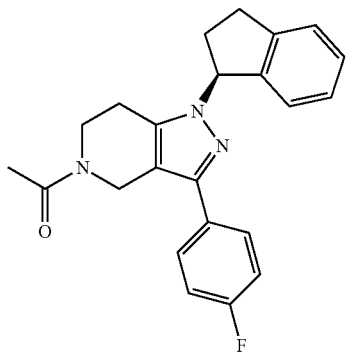 [SMILES: CC(=O)N1CCc2c(c(-c3ccc(F)cc3)nn2[C@H]2CCc3ccccc32)C1]

According to Scheme 7: In analogy to the synthesis of (12a), but taking (R)-1-indanol instead, 1-[(S)-3-(4-fluoro-phenyl)-1-indan-1-yl-1,4,6,7-tetrahydro-pyrazolo[4,3-c]pyridin-5-yl]-ethanone (12b) was obtained. R$_t$=2.46 min (LC method 6). Detected mass: 376.17 [M+H$^+$].

Example 13

1R,2R)-4,6-Difluoro-1-[3-(4-fluoro-phenyl)-4,5,6,7-tetrahydro-pyrazolo[4,3-c]pyridin-1-yl]-indan-2-ol (13a)

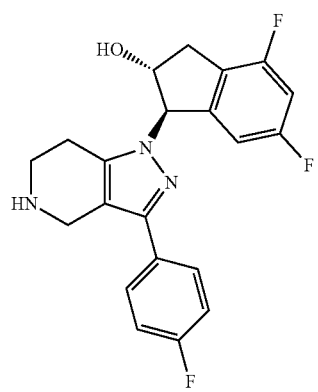 [SMILES: O[C@@H]1Cc2c(F)cc(F)cc2[C@H]1n1nc(-c2ccc(F)cc2)c2c1CCNC2]

According to Scheme 8: A mixture of (1R,2R)-4,6-difluoro-1-[3-(4-fluoro-phenyl)-5-isopropyl-4,5,6,7-tetrahydro-pyrazolo[4,3-c]pyridin-1-yl]-indan-2-ol (11ae) (0.2 g, 0.468 mmol), ethanol (14 ml) and 2N aqueous HCl (14 ml) was stirred at 80° C. for 6h. The mixture was concentrated in vacuo. After addition of aqueous saturated NaHCO$_3$, the mixture was extracted 3 times with ethyl acetate, solvents were evaporated in vacuo and the residue freeze-dried from CH$_3$CN-water to give 0.170 g of (1R,2R)-4,6-difluoro-1-[3-(4-fluoro-phenyl)-4,5,6,7-tetrahydro-pyrazolo[4,3-c]pyridin-1-yl]-indan-2-ol (13a).

R$_t$=1.04 min (LC method 4). Detected mass: 386.3 [M+H$^+$]

The compounds in the following table 5 were obtained according to Scheme 8 by following a similar reaction as used for synthesis of (13a). Reaction conditions varied slightly by reaction time (6 h-3 days), and in some cases the product was purified by purified by reverse phase HPLC (CH$_3$CN/water gradient with 0.1% trifluoroacetic acid):

TABLE 5

| Comp. No. | Product (Starting compound) | Chemical name | [M + H⁺] | R_t/[min] (LC-Meth.) |
|---|---|---|---|---|
| 13b | (11f) | (1R,2R)-4,6-Difluoro-1-[3-(4-fluoro-3-trifluoromethyl-phenyl)-4,5,6,7-tetrahydro-pyrazolo[4,3-c]pyridin-1-yl]-indan-2-ol | 454.2 | 0.99 (4) |
| 13c | (11t) | 3-[1-((1R,2R)-4,6-Difluoro-2-hydroxy-indan-1-yl)-4,5,6,7-tetrahydro-1H-pyrazolo[4,3-c]pyridin-3-yl]-benzonitrile | 393.2 | 0.90 (4) |
| 13d | (11d) | 3-[1-((1R,2R)-4-Bromo-6-fluoro-2-hydroxy-indan-1-yl)-4,5,6,7-tetrahydro-1H-pyrazolo[4,3-c]pyridin-3-yl]-benzonitrile | 453.10 | 0.88 (10) |
| 13e | (11g) | 3-[1-((1R,2R)-4,6-Dichloro-2-hydroxy-indan-1-yl)-4,5,6,7-tetrahydro-1H-pyrazolo[4,3-c]pyridin-3-yl]-benzonitrile | 425.22 | 1.62 (9) |

Example 14

3-[1-((1R,2R)-4,6-Difluoro-2-hydroxy-indan-1-yl)-5-propionyl-4,5,6,7-tetrahydro-1H-pyrazolo[4,3-c]pyridin-3-yl]-benzonitrile (14a)

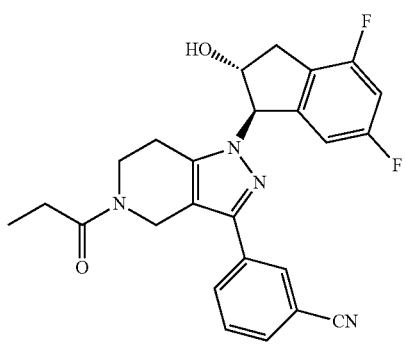 [SMILES: CCC(=O)N1CCc2c(c(-c3cccc(C#N)c3)nn2[C@@H]2c3cc(F)cc(F)c3C[C@H]2O)C1]

According to Scheme 9: To a solution of 3-[1-((1R,2R)-4,6-difluoro-2-hydroxy-indan-1-yl)-4,5,6,7-tetrahydro-1H-pyrazolo[4,3-c]pyridin-3-yl]-benzonitrile (13c) (0.05 g, 0.127 mmol) in $CH_2Cl_2$ (2 ml) at 0° C. triethylamine (19 mg, 0.191 mmol) and propionyl chloride (13 mg, 0.140 mmol) was added and the mixture was stirred for 30 min at 0-5° C. After addition of aqueous saturated $NaHCO_3$ (2 ml), the mixture was extracted with $CH_2Cl_2$ (10 ml), the organic layer was dried over $Na_2SO_4$, solvents were evaporated in vacuo and the crude product was purified by reverse phase HPLC ($CH_3CN$/water gradient with 0.1% trifluoroacetic acid) to give 15 mg of 3-[1-((1R,2R)-4,6-difluoro-2-hydroxy-indan-1-yl)-5-propionyl-4,5,6,7-tetrahydro-1H-pyrazolo[4,3-c]pyridin-3-yl]-benzonitrile (14a).

$R_t$=1.24 min (LC method 4). Detected mass: 449.18 $[M+H^+]$.

The examples in the following table 6 were obtained according to Scheme 9 by following a similar reaction according to the synthesis of (14a). Reaction conditions varied slightly by reaction time (1 h-18 h), and reaction temperature (0° C.-25° C.).

TABLE 6

| Comp. No. | Product (Starting compounds) | Chemical name | $[M + H^+]$ | $R_t$/[min] (LC-Meth.) |
|---|---|---|---|---|
| 14b | (13c + cylopropanecarbonyl-chloride) | 3-[5-Cyclopropanecarbonyl-1-((1R,2R)-4,6-difluoro-2-hydroxy-indan-1-yl)-4,5,6,7-tetrahydro-1H-pyrazolo[4,3-c]pyridin-3-yl]-benzonitrile | 461.26 | 1.13 (1) |
| 14c | (13c + isobutyrylchloride) | 3-[1-((1R,2R)-4,6-Difluoro-2-hydroxy-indan-1-yl)-5-isobutyryl-4,5,6,7-tetrahydro-1H-pyrazolo[4,3-c]pyridin-3-yl]-benzonitrile | 463.2 | 1.26 (4) |

TABLE 6-continued

| Comp. No. | Product (Starting compounds) | Chemical name | [M + H⁺] | R_t[min] (LC-Meth.) |
|---|---|---|---|---|
| 14d | (13c + pivaloylchloride) | 3-[1-((1R,2R)-4,6-Difluoro-2-hydroxy-indan-1-yl)-5-(2,2-dimethyl-propionyl)-4,5,6,7-tetrahydro-1H-pyrazolo[4,3-c]pyridin-3-yl]-benzonitrile | 477.22 | 1.3 (4) |
| 14e | (13c + methoxyacetylchloride) | 3-[1-((1R,2R)-4,6-Difluoro-2-hydroxy-indan-1-yl)-5-(2-methoxy-acetyl)-4,5,6,7-tetrahydro-1H-pyrazolo[4,3-c]pyridin-3-yl]-benzonitrile | 465.17 | 1.2 (4) |

Examples 15

The example compounds in the following table 7 were obtained as by-product during the synthesis of compound 14a and 14b respectively.

TABLE 7

| Comp. No. | Product (by-product of) | Chemical name | [M + H⁺] | R_t[min] (LC-Meth.) |
|---|---|---|---|---|
| 15a | | Propionic acid (1R,2R)-1-[3-(3-cyano-phenyl)-5-propionyl-4,5,6,7-tetrahydro-pyrazolo[4,3-c]pyridin-1-yl]-4,6-difluoro-indan-2-yl ester | 505.23 | 1.34 (4) |

TABLE 7-continued

| Comp. No. | Product (by-product of) | Chemical name | [M + H⁺] | $R_t$[min] (LC-Meth.) |
|---|---|---|---|---|
| 15b | (structure) | 3-[5-Cyclopropanecarbonyl-1-((1R,2R)-4,6-difluoro-2-hydroxy-indan-1-yl)-4,5,6,7-tetrahydro-1H-pyrazolo[4,3-c]pyridin-3-yl]-benzamide | 479.21 | 1.12 (4) |

Example 16

3-[5-Acetyl-1-((1R,2R)-4,6-difluoro-2-methoxy-indan-1-yl)-4,5,6,7-tetrahydro-1H-pyrazolo[4,3-c]pyridin-3-yl]-benzonitrile (16a)

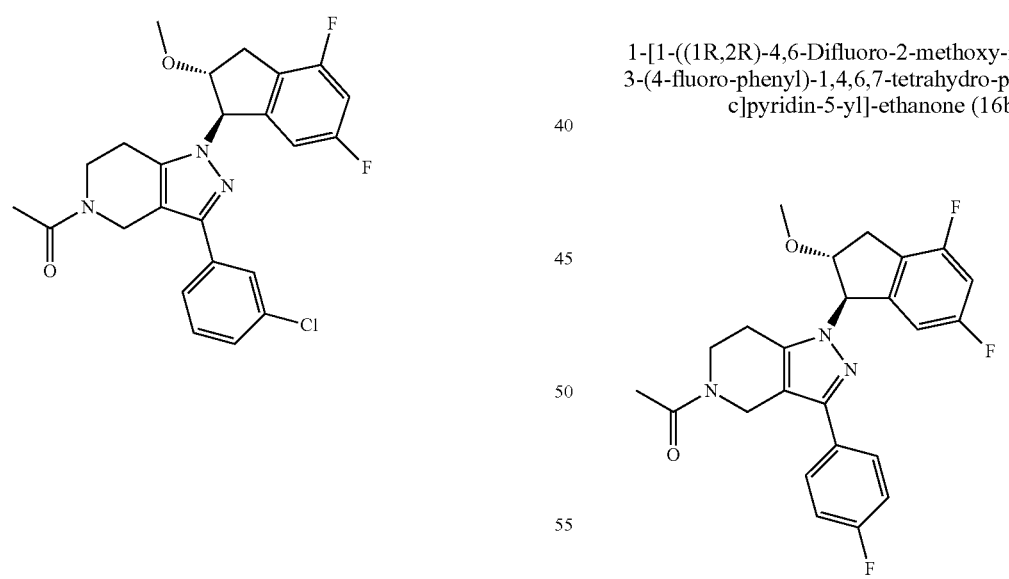

According to Scheme 10: To a solution of 3-[5-acetyl-1-((1R,2R)-4,6-difluoro-2-hydroxy-indan-1-yl)-4,5,6,7-tetrahydro-1H-pyrazolo[4,3-c]pyridin-3-yl]-benzonitrile (11t) (0.10 g, 0.276 mmol) in dry DMF (1 ml) at −10° C. NaHMDS (50 mg) was added. After 5 min iodomethane (39 mg, 0.276 mmol) was added and the mixture was allowed to warm to 25° C. After 90 min the mixture was cooled to −10° C. and the same amount of both NaHMDS and iodomethane was added again. After stirring overnight the mixture was purified by reverse phase HPLC (CH₃CN/water gradient with 0.1% trifluoroacetic acid) to give 27 mg of 3-[5-acetyl-1-((1R,2R)-4,6-difluoro-2-methoxy-indan-1-yl)-4,5,6,7-tetrahydro-1H-pyrazolo[4,3-c]pyridin-3-yl]-benzonitrile (16a). $R_t$=1.29 min (LC method 4). Detected mass: 449.32 [M+H⁺]

1-[1-((1R,2R)-4,6-Difluoro-2-methoxy-indan-1-yl)-3-(4-fluoro-phenyl)-1,4,6,7-tetrahydro-pyrazolo[4,3-c]pyridin-5-yl]-ethanone (16b)

According to Scheme 10: 1-[1-((1R,2R)-4,6-Difluoro-2-methoxy-indan-1-yl)-3-(4-fluoro-phenyl)-1,4,6,7-tetrahydro-pyrazolo[4,3-c]pyridin-5-yl]-ethanone (16b) was obtained by following a reaction according to synthesis of (16a). $R_t$=1.32 min (LC method 4). Detected mass: 442.28 [M+H⁺].

Example 17

3-(3-Cyano-phenyl)-1-((1R,2R)-4,6-difluoro-2-hydroxy-indan-1-yl)-1,4,6,7-tetrahydro-pyrazolo[4,3-c]pyridine-5-carboxylic acid methyl ester (17a)

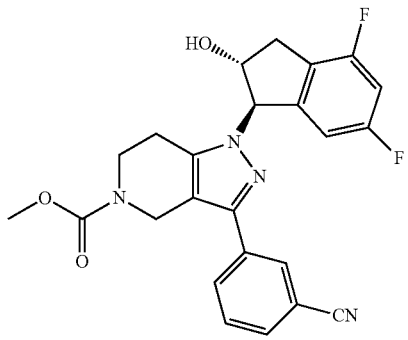 [SMILES: COC(=O)N1CCc2c(c(-c3cccc(C#N)c3)nn2[C@@H]2c3cc(F)cc(F)c3C[C@H]2O)C1]

According to Scheme 11: To a solution of 3-[1-((1R,2R)-4,6-difluoro-2-hydroxy-indan-1-yl)-4,5,6,7-tetrahydro-1H-pyrazolo[4,3-c]pyridin-3-yl]-benzonitrile (11t) (0.05 g, 0.123 mmol) in dry $CH_2Cl_2$ (2 ml) at 0° C. methyl chloroformate (12 mg, 0.13 mmol) and $NEt_3$ (19 mg, 0.191 mmol) was added, the mixture was stirred at 0-5° C. for 60 min, then at 25° C. for 18 h. After addition of aqueous saturated $NaHCO_3$ (2 ml), the mixture was extracted with $CH_2Cl_2$ (10 ml), the organic layer was dried over $Na_2SO_4$, solvents were evaporated in vacuo and the crude product was purified by purified by reverse phase HPLC ($CH_3CN$/water gradient with 0.1% trifluoroacetic acid) to give 31 mg of 3-(3-cyano-phenyl)-1-((1R,2R)-4,6-difluoro-2-hydroxy-indan-1-yl)-1,4,6,7-tetrahydro-pyrazolo[4,3-c]pyridine-5-carboxylic acid methyl ester (17a).

$R_t$=1.27 min (LC method 4). Detected mass: 451.17 $[M+H^+]$.

Example 18

1R,2R)-1-[5-Cyclopropylmethyl-3-(4-fluoro-phenyl)-4,5,6,7-tetrahydro-pyrazolo[4,3-c]pyridin-1-yl]-4,6-difluoro-indan-2-ol, hydrochloride salt (18a

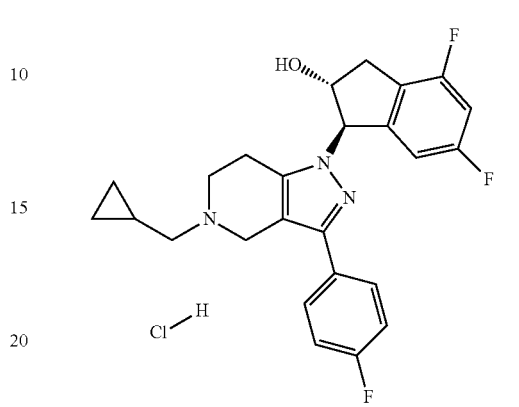

According to Scheme 12: A mixture of (1R,2R)-4,6-difluoro-1-[3-(4-fluoro-phenyl)-4,5,6,7-tetrahydro-pyrazolo[4,3-c]pyridin-1-yl]-indan-2-ol (13a) (0.05 g, 0.13 mmol), NEt3 (39 mg, 0.389 mmol) and cyclopropylmethyl bromide (21 mg, 0.155 mmol) in N,N-dimethylformamide was stirred at 90° C. for 18 h. The mixture was purified by reverse phase HPLC ($CH_3CN$/water gradient with 0.1% trifluoroacetic acid). After addition of aqueous $NaHCO_3$ the solution was extracted with ethyl acetate, the organic layer evaporated to dryness, redissolved in $CH_3CN$ and aqueous 2 M HCl and freeze-dried to give 31 mg of (1R,2R)-1-[5-cyclopropylmethyl-3-(4-fluoro-phenyl)-4,5,6,7-tetrahydro-pyrazolo[4,3-c]pyridin-1-yl]-4,6-difluoro-indan-2-ol, hydrochloride salt (18a).

$R_t$=1.09 min (LC method 4). Detected mass: 440.34 $[M+H^+]$.

The examples in the following table 8 were obtained according to Scheme 12 by following a reaction according to the synthesis of (18a). Sometimes, $CH_3CN$ was used instead of DMF and the temperature was decreased to 50° C.

TABLE 8

| Comp. No. | Product (Starting compounds) | Chemical name | $[M + H^+]$ | $R_t$/[min] (LC-Meth.) |
|---|---|---|---|---|
| 18b | (13a + isopropylbromide) | (1R,2R)-4,6-Difluoro-1-[3-(4-fluoro-phenyl)-5-isopropyl-4,5,6,7-tetrahydro-pyrazolo[4,3-c]pyridin-1-yl]-indan-2-ol | 428.33 | 3.33 (2) |

TABLE 8-continued

| Comp. No. | Product (Starting compounds) | Chemical name | [M + H⁺] | R$_t$/[min] (LC-Meth.) |
|---|---|---|---|---|
| 18c | 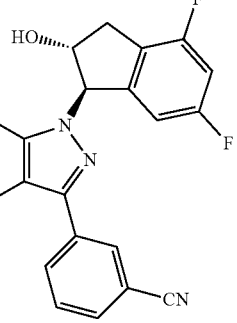<br>(13c + 1-iodo-3,3,3-trifluoro-propane (CH₃CN/50° C.)) | 3-[1-((1R,2R)-4,6-Difluoro-2-hydroxy-indan-1-yl)-5-(3,3,3-trifluoro-propyl)-4,5,6,7-tetrahydro-1H-pyrazolo[4,3-c]pyridin-3-yl]-benzonitrile | 489.15 | 1.14 (4) |
| 18d | 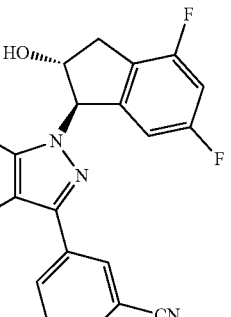<br>13c + 2-bromoethylmethyl ether | 3-[1-((1R,2R)-4,6-Difluoro-2-hydroxy-indan-1-yl)-5-(2-methoxy-ethyl)-4,5,6,7-tetrahydro-1H-pyrazolo[4,3-c]pyridin-3-yl]-benzonitrile; HCl salt | 451.23 | 1.05 (4) |
| 18e | 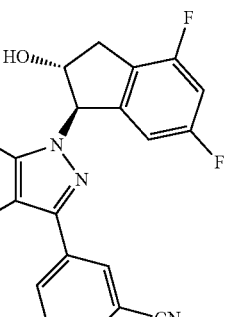<br>(13c + cyclopropylmethylbromide) | 3-[5-Cyclopropylmethyl-1-((1R,2R)-4,6-difluoro-2-hydroxy-indan-1-yl)-4,5,6,7-tetrahydro-1H-pyrazolo[4,3-c]pyridin-3-yl]-benzonitrile; HCl salt | 447.23 | 1.07 (4) |

TABLE 8-continued

| Comp. No. | Product (Starting compounds) | Chemical name | [M + H⁺] | R$_t$/[min] (LC-Meth.) |
|---|---|---|---|---|
| 18f | 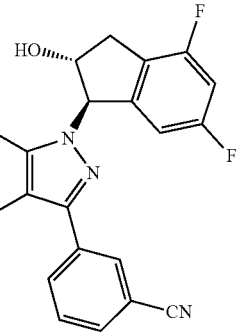<br>(13c + 1-bromopropane) | (1R,2R)-4,6-Difluoro-1-[3-(4-fluoro-phenyl)-5-propyl-4,5,6,7-tetrahydro-pyrazolo[4,3-c]pyridin-1-yl]-indan-2-ol; HCl salt | 428.36 | 1.08 (4) |
| 18g | 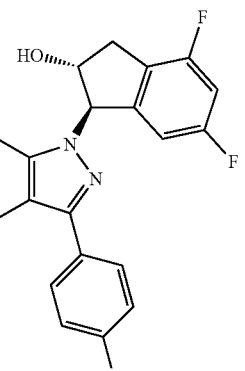<br>(13a + 2-bromoethylmethylether) | (1R,2R)-4,6-Difluoro-1-[3-(4-fluoro-phenyl)-5-(2-methoxy-ethyl)-4,5,6,7-tetrahydro-pyrazolo[4,3-c]pyridin-1-yl]-(indan-2-ol; HCl salt | 444.35 | 1.07 (4) |

The example in the following table 9 is obtained as by-products during the synthesis of compounds 18c.

TABLE 9

| Comp. No. | Product | Chemical name | [M + H⁺] | R$_t$/[min] (LC-Meth.) |
|---|---|---|---|---|
| 18h | 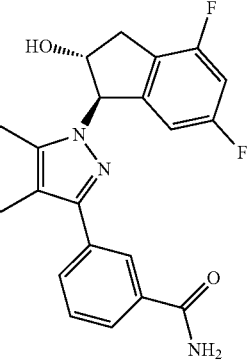 | 3-[1-((1R,2R)-4,6-Difluoro-2-hydroxy-indan-1-yl)-5-(3,3,3-trifluoro-propyl)-4,5,6,7-tetrahydro-1H-pyrazolo[4,3-c]pyridin-3-yl]-benzamide; compound with trifluoro-acetic acid | 507.15 | 1.01 (4) |

Example 19

3-[5-Acetyl-1-((1R,2R)-6-fluoro-2-hydroxy-4-methyl-indan-1-yl)-4,5,6,7-tetrahydro-1H-pyrazolo[4,3-c]pyridin-3-yl]-benzonitrile (19a)

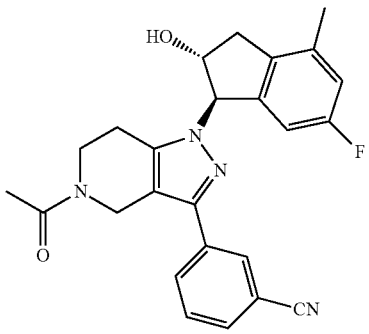 [SMILES: CC(=O)N1CCc2c(c(-c3cccc(C#N)c3)nn2[C@@H]2c3cc(F)cc(C)c3C[C@H]2O)C1]

According to Scheme 13: A mixture of 3-[5-acetyl-1-((1R,2R)-4-bromo-6-fluoro-2-hydroxy-indan-1-yl)-4,5,6,7-tetrahydro-1H-pyrazolo[4,3-c]pyridin-3-yl]-benzonitrile (11d) (0.05 g, 0.10 mmol), tetramethyltin (101 mg, 0.566 mmol) and tetrakis(triphenylphosphine)palladium(0) (6 mg, 0.005 mmol) in N,N-dimethylformamide (2 ml) was stirred at 110° C. for 18 h. The mixture was purified by reverse phase HPLC (CH$_3$CN/water gradient with 0.1% trifluoroacetic acid) to give 23 mg of 3-[5-acetyl-1-((1R,2R)-6-fluoro-2-hydroxy-4-methyl-indan-1-yl)-4,5,6,7-tetrahydro-1H-pyrazolo[4,3-c]pyridin-3-yl]-benzonitrile (19a).

$R_t$=1.21 min (LC method 1). Detected mass: 431.17 [M+H$^+$].

3-[5-Acetyl-1-((1R,2R)-4-ethyl-6-fluoro-2-hydroxy-indan-1-yl)-4,5,6,7-tetrahydro-1H-pyrazolo[4,3-c]pyridin-3-yl]-benzonitrile (19b)

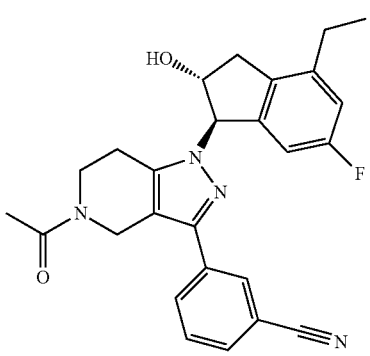 [SMILES: CCc1cc(F)cc2c1C[C@@H](O)[C@@H]2n1nc(-c2cccc(C#N)c2)c2c1CCN(C(C)=O)C2]

According to Scheme 13: 3-[5-acetyl-1-((1R,2R)-4-ethyl-6-fluoro-2-hydroxy-indan-1-yl)-4,5,6,7-tetrahydro-1H-pyrazolo[4,3-c]pyridin-3-yl]-benzonitrile (19b) was obtained by following a reaction according to the synthesis of (19a), but using tetraethyltin instead of tetramethyltin.

$R_t$=1.25 min (LC method 1). Detected mass: 445.18 [M+H$^+$].

Example 20

3-[5-Acetyl-1-((1R,2R)-4-cyclopropyl-6-fluoro-2-hydroxy-indan-1-yl)-4,5,6,7-tetrahydro-1H-pyrazolo[4,3-c]pyridin-3-yl]-benzonitrile (20a)

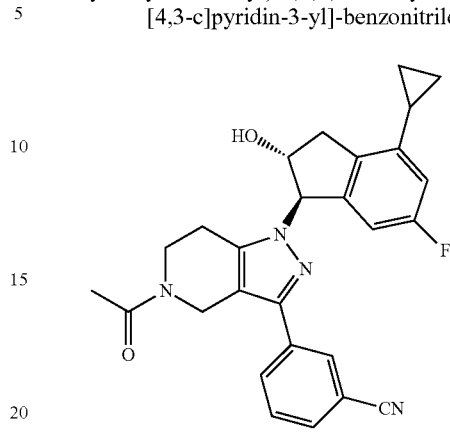

According to Scheme 14: A mixture of cyclopropylboronic acid (28 mg, 0.33 mmol), 3-[5-acetyl-1-((1R,2R)-4-bromo-6-fluoro-2-hydroxy-indan-1-yl)-4,5,6,7-tetrahydro-1H-pyrazolo[4,3-c]pyridin-3-yl]-benzonitrile (11d) (0.05 g, 0.10 mmol), K$_2$CO$_3$ (83 mg, 0.606 mmol) and tetrakis(triphenylphosphine)palladium(0) (17 mg, 0.005, 0.015 mmol) in CH$_3$CN (2 ml) and water (0.75 ml) was stirred at 110° C. for 2 h under microwave irradiation. The mixture was purified by reverse phase HPLC (CH$_3$CN/water gradient with 0.1% trifluoroacetic acid) to give 9 mg of 3-[5-acetyl-1-((1R,2R)-4-cyclopropyl-6-fluoro-2-hydroxy-indan-1-yl)-4,5,6,7-tetrahydro-1H-pyrazolo[4,3-c]pyridin-3-yl]-benzonitrile (20a).

$R_t$=1.25 min (LC method 4). Detected mass: 457.15 [M+H$^+$].

Example 21

3-[5-Acetyl-1-((1R,2R)-4-chloro-6-fluoro-2-hydroxy-indan-1-yl)-4,5,6,7-tetrahydro-1H-pyrazolo[4,3-c]pyridin-3-yl]-benzonitrile (21a)

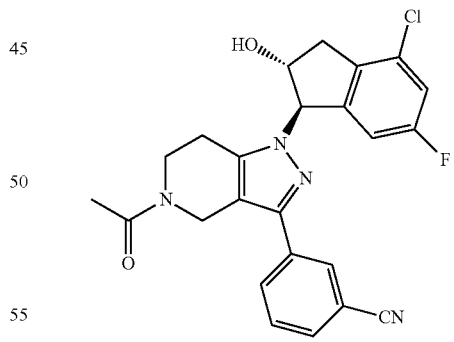

According to Scheme 15: A mixture of 3-[5-acetyl-1-((1R,2R)-4-bromo-6-fluoro-2-hydroxy-indan-1-yl)-4,5,6,7-tetrahydro-1H-pyrazolo[4,3-c]pyridin-3-yl]-benzonitrile (11d) (0.15 g, 0.303 mmol) and CuCl (60 mg, 0.606 mmol) in dimethylsulfoxide (2 ml) was stirred at 180° C. for 90 min under microwave irradiation. The mixture was purified by reverse phase HPLC (CH$_3$CN/water gradient with 0.1% trifluoroacetic acid) to give 15 mg of 3-[5-acetyl-1-((1R,2R)-4-chloro-6-fluoro-2-hydroxy-indan-1-yl)-4,5,6,7-tetrahydro-1H-pyrazolo[4,3-c]pyridin-3-yl]-benzonitrile (21a).

$R_t$=1.23 min (LC method 4). Detected mass: 451.09 [M+H$^+$].

(1R,2R)-1-[5-Acetyl-3-(3-cyano-phenyl)-4,5,6,7-tetrahydro-pyrazolo[4,3-c]pyridin-1-yl]-6-fluoro-2-hydroxy-indan-4-carbonitrile (21b)

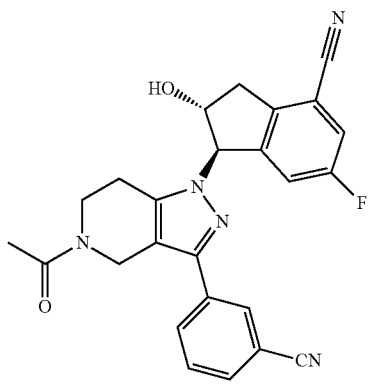 [SMILES: CC(=O)N1CCc2c(c(-c3cccc(C#N)c3)nn2[C@@H]2c3cc(F)cc(C#N)c3C[C@H]2O)C1]

According to Scheme 15: A mixture of 3-[5-acetyl-1-((1R,2R)-4-bromo-6-fluoro-2-hydroxy-indan-1-yl)-4,5,6,7-tetrahydro-1H-pyrazolo[4,3-c]pyridin-3-yl]-benzonitrile (11d) (0.15 g, 0.303 mmol) and CuCN (54 mg, 0.606 mmol) in dimethylsulfoxide (2 ml) was stirred at 180° C. for 90 min under microwave irradiation. The mixture was purified by reverse phase HPLC (CH$_3$CN/water gradient with 0.1% trifluoroacetic acid) to give 27 mg of (1R,2R)-1-[5-acetyl-3-(3-cyano-phenyl)-4,5,6,7-tetrahydro-pyrazolo[4,3-c]pyridin-1-yl]-6-fluoro-2-hydroxy-indan-4-carbonitrile (21b). $R_t$=1.16 min (LC method 4). Detected mass: 442.12 [M+H$^+$].

3-[5-Acetyl-1-((1R,2R)-6-fluoro-2-hydroxy-4-methylsulfanyl-indan-1-yl)-4,5,6,7-tetrahydro-1H-pyrazolo[4,3-c]pyridin-3-yl]-benzonitrile (21c)

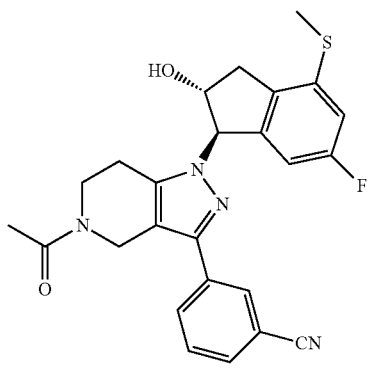 [SMILES: CSc1cc(F)cc2c1C[C@@H](O)[C@@H]2n1nc(-c2cccc(C#N)c2)c2c1CCN(C(C)=O)C2]

According to Scheme 15: 10 mg of 3-[5-acetyl-1-((1R,2R)-6-fluoro-2-hydroxy-4-methylsulfanyl-indan-1-yl)-4,5,6,7-tetrahydro-1H-pyrazolo[4,3-c]pyridin-3-yl]-benzonitrile (21c) were obtained as by-product during the synthesis of (21b).

$R_t$=1.22 min (LC method 4). Detected mass: 463.12 [M+H$^+$].

Example 22

3-(3-Cyano-phenyl)-1-((1R,2R)-4,6-dichloro-2-hydroxy-indan-1-yl)-1,4,6,7-tetrahydro-pyrazolo[4,3-c]pyridine-5-carboxylic acid ethylamide (22a)

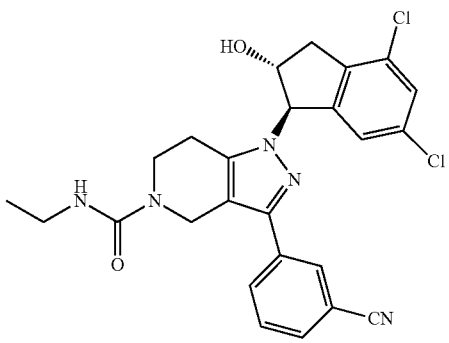 [SMILES: CCNC(=O)N1CCc2c(c(-c3cccc(C#N)c3)nn2[C@@H]2c3cc(Cl)cc(Cl)c3C[C@H]2O)C1]

According to Scheme 17: To a solution of 3-[1-((1R,2R)-4,6-dichloro-2-hydroxy-indan-1-yl)-4,5,6,7-tetrahydro-1H-pyrazolo[4,3-c]pyridin-3-yl]-benzonitrile (13e) (0.03 g, 0.071 mmol) in dry CH$_2$Cl$_2$ at 0° C. triethylamine (57 mg, 0.564 mmol) and ethylisocyanate (5.5 mg, 0.077 mmol) was added. The mixture was stirred for 1 h at room temperature and purified by reverse phase HPLC (CH$_3$CN/water gradient with 0.1% trifluoroacetic acid) to give 31 mg of 3-(3-cyano-phenyl)-1-((1R,2R)-4,6-dichloro-2-hydroxy-indan-1-yl)-1,4,6,7-tetrahydro-pyrazolo[4,3-c]pyridine-5-carboxylic acid ethylamide (22a)

$R_t$=1.99 min (LC method 9). Detected mass: 496.31 [M+H$^+$].

Example 23

3-[1-((1R,2R)-4,6-Dichloro-2-hydroxy-indan-1-yl)-5-methanesulfonyl-4,5,6,7-tetrahydro-1H-pyrazolo[4,3-c]pyridin-3-yl]-benzonitrile (23a)

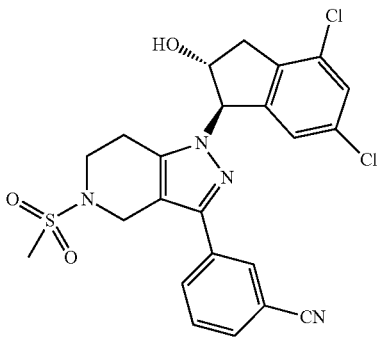 [SMILES: CS(=O)(=O)N1CCc2c(c(-c3cccc(C#N)c3)nn2[C@@H]2c3cc(Cl)cc(Cl)c3C[C@H]2O)C1]

To a solution of 3-[1-((1R,2R)-4,6-Dichloro-2-hydroxy-indan-1-yl)-4,5,6,7-tetrahydro-1H-pyrazolo[4,3-c]pyridin-3-yl]-benzonitrile (13e) (0.02 g, 0.047 mmol) in dry tetrahydrofuran at −70° C. was added slowly and portionwise 100 µl of a solution of methanesulfonyl chloride (100 µl in 10 ml dry tetrahydrofuran) and after 5 min triethylamine (21 mg, 0.208 mmol). The mixture was stirred at −70° C. for 15 min and then a second portion of the methanesulfonyl/tetrahydrofuran solution above was added (100 µl). The mixture was stirred at −70° C. for 15 min and then a third portion of the methanesulfonyl/tetrahydrofuran solution above was added (50 μl). The mixture was stirred at −70° C. for 3 min, quenched with aqueous NaHCO$_3$ and extracted 3 times with CH$_2$Cl$_2$. The combined organic layers were evaporated to dryness and the residue was purified by reverse phase HPLC (CH$_3$CN/water gradient with 0.1% trifluoroacetic acid) to give 15 mg of 3-[1-((1R,2R)-4,6-Dichloro-2-hydroxy-indan-1-yl)-5-methanesulfonyl-4,5,6,7-tetrahydro-1H-pyrazolo[4,3-c]pyridin-3-yl]-benzonitrile (23a).

R$_t$=2.00 min (LC method 9). Detected mass: 503.12 [M+H$^+$].

The following LC methods were used to analyze the exemplary embodiments:

The following abbreviations are used for formic acid FA, for trifluoroacetic acid TFA and for acetonitrile ACN.

LC method 1:
Stationary phase: Waters UPLC BEH C18 2.1*50 mm; 1.7μ
Gradient: H$_2$O+0.05% FA:ACN+0.035% FA 95:5 (0 min) to 5:95 (1.1 min) to 5:95 (1.7 min) to 95:5 (1.9 min) to 95:5 (2 min)
Flow: 0.9 ml/min, 55° C.

LC method 2:
Gradient: H$_2$O+0.1% FA:ACN+0.1% FA 97:3 (0 min) to 40:60 (3.5 min) to 2:98 (4 min) to 2:98 (5 min) to 97:3 (5.2 min) to 97:3 (6.5 min);
Flow: 1.3 mL/min LC method 3:
Stationary phase: Waters XBridge C18, 4.6*50; 2.5μ
Gradient: H$_2$O+0.05% TFA:ACN+0.05% TFA 95:5 (0 min) to 95:5 (0.2 min) to 5:95 (2.4 min) to 5:95 (3.2 min) to 95:5 (3.3 min) to 95:5 (4.0 min)
Flow: 1.7 ml/min, 40° C.

LC method 4:
Stationary phase: Waters UPLC BEH C18 2, 1*50 mm; 1.7μ
Gradient: H$_2$O+0.1% FA:ACN+0.08% FA 95:5 (0 min) to 5:95 (1.1 min) to 5:95 (1.7 min) to 95:5 (1.8 min) to 95:5 (2 min)
Flow: 0.9 ml/min 55° C.

LC method 5:
Stationary phase: Waters XBridge C18, 4.6*50, 2.5μ
Gradient: H$_2$O+0.05% TFA:ACN+0.05% TFA 95:5 (0 min) to 95:5 (0.2 min) to 5:95 (2.4 min) to 5:95 (3.5 min) to 95:5 (3.6 min) to 95:5 (4.5 min)
Flow: 1.7 ml/min, 50° C.

LC method 6:
Stationary phase: Waters XBridge C18, 4.6*50, 2.5μ
Gradient: H$_2$O+0.05% TFA:ACN+0.05% TFA 95:5 (0 min) to 5:95 (2.6 min) to 5:95 (3.0 min) to 95:5 (3.1 min) to 95:5 (4.0 min)
Flow: 1.7 ml/min, 40° C.

LC method 7:
Stationary phase: Merck Chromolith fast Grad RP/18e, 50×2 mm
Gradient: H$_2$O+0.05% TFA:ACN+0.05% TFA 98:2 (0 min) to 98:2 (0.2 min) to 2:98 (2.4 min) to 2:98 (3.2 min) to 98:2 (3.3 min) to 98:2 (4 min)
Flow: 2 ml/min, 50° C.

LC method 8:
Stationary phase: Waters XBridge C18, 4.6*50, 2.5μ.
Gradient: H$_2$O+0.05% TFA:ACN+0.05% TFA 95:5 (0 min) to 95:5 (0.3 min) to 5:95 (3.5 min) to 5:95 (4 min) Flow: 1.3 ml/min, 40° C.

LC method 9:
Stationary phase: Waters UPLC BEH C18 2, 1*50 mm; 1.7μ.
Gradient: H$_2$O+0.05% FA:ACN+0.035% FA 98:2 (0 min) to 5:95 (2 min) to 5:95 (2.6 min) to 95:5 (2.7 min) to 95:5 (3 min)
Flow: 0.9 ml/min 55°

LC method 10:
Stationary phase: 0.2 μl 10×2 0 Luna C18.3μ.
Gradient: 0 min 93% H$_2$O (0.05% TFA)—1.0 min-95% ACN; 95% ACN to 1.45 min; 7% ACN 1.50 min
Flow: 1 ml/min 55°

Determination of the activity on the TASK-1 channel in *Xenopus* oocytes:

Human TASK-1 channels were expressed in *Xenopus* oocytes. For this purpose, oocytes were isolated from *Xenopus laevis* and defolliculated. Subsequently, TASK-1-encoding RNA synthesized in vitro was injected into oocytes. After two days of TASK-1 protein expression, TASK-1 currents were measured by two-microelectrode voltage clamp. Data were acquired and analyzed using a TEC-10cx amplifier (NPI Electronic, Tamm, Germany) connected to an ITC-16 interface (Instrutech Corp., Long Island, USA) and Pulse software (HEKA Elektronik, Lambrecht, Germany). Oocytes were clamped to −90 mV and TASK-1 mediated currents were measured during 500 ms voltage pulses to 40 mV. Oocytes were continuously superfused with ND96 buffer containing: NaCl 96 mM, KCl$_2$ mM, CaCl$_2$ 1.8 mM, MgCl$_2$ 1 mM, HEPES 5 mM (pH adjusted to 7.4 with NaOH). All experiments were performed at room temperature.

Test substances were consecutively added to the bath solution at rising concentrations. Compound effects were calculated as the percentage inhibition of TASK-1 control current before compound application. IC$_{50}$ values were obtained by fitting the data to the general dose-response equation.

The following products/compounds were tested in said assay by using the respective form (salt or free base) obtained as in the examples described above and the following activities were measured (IC$_{50}$ (table 10) or Inhibition % at 5 μM (table 11)):

TABLE 10

| Example No. | IC$_{50}$ (μM) |
| --- | --- |
| 11a | 0.171 |
| 11b | 0.19 |
| 11c | 0.204 |
| 11d | 0.226 |
| 11e | 0.239 |
| 11f | 0.27 |
| 11g | 0.35 |
| 11h | 0.37 |
| 11i | 0.375 |
| 11j | 0.439 |
| 11k | 0.442 |
| 11l | 0.495 |
| 11m | 0.518 |
| 11n | 0.568 |
| 11o | 0.675 |
| 11p | 0.685 |
| 11q | 0.773 |
| 11r | 0.789 |
| 11s | 0.804 |
| 11t | 0.881 |
| 11u | 1.01 |
| 11v | 1.185 |
| 11w | 1.26 |
| 11x | 1.517 |
| 11y | 1.915 |
| 11z | 2.132 |

TABLE 10-continued

| Example No. | IC$_{50}$ (μM) |
| --- | --- |
| 11aa | 2.219 |
| 11ab | 2.974 |
| 11ac | 3.879 |
| 11ad | 6.886 |
| 12a | 0.712 |
| 12b | 0.479 |
| 14a | 0.07 |
| 14b | 0.0831 |
| 14c | 0.25 |
| 16a | 0.446 |
| 16b | 1.164 |
| 17a | 0.26 |
| 18a | 0.5 |
| 18b | 8.192 |
| 19a | 0.231 |
| 20a | 0.5 |
| 21a | 0.393 |
| 22a | 0.18 |

TABLE 11

| Example No. | Inhibition % (5 μM) |
| --- | --- |
| 11ae | 61% |
| 14d | 94% |
| 14e | 72% |
| 15a | 51% |
| 15b | 24% |
| 18c | 91% |
| 18d | 83% |
| 18e | 81% |
| 18f | 67% |
| 18g | 56% |
| 18h | 39% |
| 19b | 82% |
| 21c | 87% |
| 23a | 80% |

Investigation of the refractory period and the left-atrial vulnerability in the pig:

The compounds were tested for prolongation of the refractory period and antiarrhythmic activity on the atrium of the anesthetized pig as described in the literature (Knobloch et al. 2002. Naunyn-Schmiedberg's Arch. Pharmacol. 366; 482-487). Here the anti-arrhythmic action relates to the inhibition of the occurrence of episodes of arrhythmias which are induced by a prematurely placed extra-stimulus (S2) in the left atrium (=left-atrial vulnerability). The refractory period values are stated in percent of the basal values 15 minutes after injection. Mean values for the refractory periods are shown from three rates (150, 200 and 250/min). The inhibitory values for the inhibition of episodes of arrhythmias refer to 3 measurements (3 timepoints) before administration vs. 3 measurements during the first hour after administration of the compounds.

The action of 3-[5-Acetyl-1-((1R,2R)-6-chloro-4-fluoro-2-hydroxy-indan-1-yl)-4,5,6,7-tetrahydro-1H-pyrazolo[4,3-c]pyridin-3-yl]-benzonitrile (11j) on the refractory period of the left atrium and antiarrhythmic activity in the anesthetized pig after a bolus administration of 1 mg/kg is shown in table 12. From the results shown in table 12, it is seen that it was possible to prevent 82% of the induced arrhythmias.

TABLE 12

| | Mean value |
| --- | --- |
| % increase in the refractory period | 20% |
| % inhibition of the arrhythmias | 82% |
| Number of animals | n = 2 |

The invention claimed is:
1. A compound of the formula I,

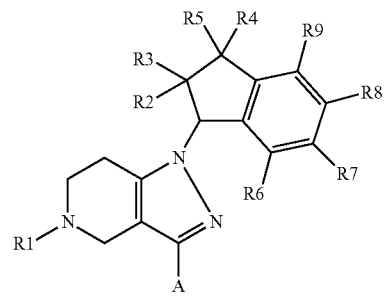

wherein
A is $(C_6-C_{10})$-aryl or five-membered or six-membered heteroaryl, comprising 1-3 heteroatoms selected from N, O and S,
wherein aryl and heteroaryl are optionally substituted with 1-3 substituents selected independently from F, Cl, Br, $(C_1-C_6)$-alkyl, $(C_1-C_6)$-alkyloxy-, $(C_1-C_6)$-alkyl-S—, NC—, $(C_1-C_6)$-alkyl-OC(O)—, $(C_1-C_6)$-alkyl-SO$_2$—, $(C_1-C_6)$-alkyloxy-$(C_1-C_6)$-alkyl- and $R^{12}R^{13}N$—C(O)—,
wherein one or more hydrogen atoms of the alkyl moieties are optionally replaced by fluorine;
R1 is $R^{10}$—C(O)—, $R^{11}$—$(C_1-C_6)$-alkyl, $(C_3-C_6)$-cycloalkyl, $(C_1-C_6)$-alkyl-SO$_2$— or $R^{12}R^{13}N$—C(O)—$(C_1-C_6)$-alkyl-,
wherein one or more hydrogen atoms of the alkyl moieties are optionally replaced by fluorine;
R2 is H, OH, $(C_1-C_6)$-alkyl, $(C_1-C_6)$-alkyloxy-, or $(C_1-C_6)$-alkyl-C(O)O—;
R3 is H or $(C_1-C_6)$-alkyl;
R4 is H, F or $(C_1-C_6)$-alkyl,
wherein one or more hydrogen atoms of the alkyl residue are optionally replaced by fluorine;
R5 is H, F or $(C_1-C_6)$-alkyl,
wherein one or more hydrogen atoms of the alkyl residue are optionally replaced by fluorine;
R6 to R9 are each independently selected from H, F, Cl, Br, NC—, $(C_1-C_6)$-alkyl, $(C_3-C_6)$-cycloalkyl, $(C_1-C_6)$-alkyl-SO$_2$—, $(C_1-C_6)$-alkyl-OC(O)—, $(C_1-C_6)$-alkyloxy- and $(C_1-C_6)$-alkyl-S—,
wherein one or more hydrogen atoms of the alkyl moieties are optionally replaced by fluorine;
R10 is H, $(C_1-C_6)$-alkyl, $(C_3-C_6)$-cycloalkyl, $(C_1-C_6)$-alkyloxy-, $(C_1-C_6)$-alkyl-S—, HO—$(C_1-C_6)$-alkyl-, $(C_1-C_6)$-alkyl-O—$(C_1-C_6)$-alkyl-, $(C_3-C_6)$-cycloalkyl-$(C_1-C_6)$-alkyl- or $R^{12}R^{13}N$—,
wherein one or more hydrogen atoms of the alkyl moieties are optionally replaced by fluorine,
R11 is H, $(C_3-C_6)$-cycloalkyl, OH, $(C_1-C_6)$-alkyloxy- or $(C_1-C_6)$-alkyl-S—,
wherein one or more hydrogen atoms of the alkyl moieties are optionally replaced by fluorine; and R12 and R13 are each independently H or $(C_1$-$C_6)$-alkyl;
or a stereoisomer or stereoisomeric mixture thereof, or a pharmaceutically acceptable salt thereof.

2. A compound according to claim 1, wherein
A is phenyl, furanyl, furazanyl, imidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, pyrazinyl, pyrazolinyl, pyrazolyl, pyridazinyl, pyridyl, pyrimidinyl, pyrrolyl, 1,2,3-thiadiazolyl, 1,2,4-thiadiazolyl, 1,2,5-thiadiazolyl, 1,3,4-thiadiazolyl, thiazolyl, thiophenyl, triazinyl, 1,2,3-triazolyl, 1,2,4-triazolyl, 1,2,5-triazolyl, or 1,3,4-triazolyl,
optionally substituted with 1, 2 or 3 residues selected independently from F, Cl, $(C_1$-$C_4)$-alkyloxy-, $(C_1$-$C_4)$-alkyl-S—, $(C_1$-$C_4)$-alkyl, $(C_1$-$C_4)$-alkyl-OC(O)—, $(C_1$-$C_4)$-alkyl-$SO_3$— and NC—,
wherein one or more hydrogen atoms of the alkyl moieties are optionally replaced by fluorine;
R1 is $R^{10}$—C(O)—, $R^{11}$—$(C_1$-$C_4)$-alkyl- or $(C_1$-$C_2)$-alkyl-$SO_2$—;
R2 is H, OH, $(C_1$-$C_4)$-alkyloxy- or $(C_1$-$C_4)$-alkyl-C(O)O—;
R3 is H or $(C_1$-$C_6)$-alkyl;
R4 is H, F or $(C_1$-$C_6)$-alkyl,
wherein one or more hydrogen atoms of the alkyl residue are optionally replaced by fluorine;
R5 is H, F or $(C_1$-$C_6)$-alkyl,
wherein one or more hydrogen atoms of the alkyl residue are optionally replaced by fluorine;
R6 to R9 are each independently selected from H, F, Cl, Br, NC—, $(C_1$-$C_4)$-alkyl, cyclopropyl, $(C_1$-$C_2)$-alkyl-$SO_2$—, $(C_1$-$C_4)$-alkyl-OC(O)—, $(C_1$-$C_4)$-alkyloxy- and $(C_1$-$C_4)$-alkyl-S—;
wherein one or more hydrogen atoms of the alkyl moieties are optionally replaced by fluorine;
R10 is $(C_1$-$C_4)$-alkyl, cyclopropyl, $(C_1$-$C_4)$-alkyloxy, $(C_1$-$C_4)$-alkyl-S—, HO—$(C_1$-$C_4)$-alkyl-, $(C_1$-$C_4)$-alkyl-O—$(C_1$-$C_4)$-alkyl-, cyclopropyl-$(C_1$-$C_4)$-alkyl- or $R^{12}R^{13}N$—;
R11 is H, cyclopropyl, OH, $(C_1$-$C_4)$-alkyloxy- or $(C_1$-$C_4)$-alkyl-S—,
wherein one or more hydrogen atoms of the alkyl moieties are optionally replaced by fluorine; and
R12 and R13 are each independently H or $(C_1$-$C_4)$-alkyl;
or a stereoisomer or stereoisomeric mixture thereof, or a pharmaceutically acceptable salt thereof.

3. A compound according to claim 1, wherein
A is phenyl, pyridyl, pyrazinyl, pyridazinyl, pyrimidinyl, pyrazolyl, imidazolyl, isothiazolyl, thiazolyl, or thiophenyl,
optionally substituted with 1, 2 or 3 residues selected independently from F, Cl, methoxy, ethoxy, methyl, ethyl, NC—, $CF_3O$— and $CF_3$;
R1 is $R^{10}$—C(O)—, $R^{11}$—$(C_1$-$C_4)$-alkyl- or $CH_3$—$SO_2$—;
R2 is OH, methoxy, ethoxy, methyl-C(O)O— or ethyl-C(O)O—;
R3 is H or methyl;
R4 and R5 are H;
R6, R7, R8 and R9 are each independently selected from H, F, Cl, Br, NC—, methyl, ethyl, cyclopropyl, methoxy, ethoxy, methyl-S—, ethyl-S— and $CF_3$;
R10 is methyl, ethyl, n-propyl, isopropyl, n-butyl, isobutyl, sec-butyl, tert-butyl, cyclopropyl, methoxy, ethoxy, $(C_1$-$C_2)$-alkyl-O—$(C_1$-$C_2)$-alkyl-, cyclopropyl-$(C_1$-$C_2)$-alkyl- or $R^{12}R^{13}N$—;
R11 is H, cyclopropyl, methoxy, ethoxy or $CF_3$; and
R12 and R13 are each independently H, methyl or ethyl;
or a stereoisomer or stereoisomeric mixture thereof, or a pharmaceutically acceptable salt thereof.

4. A compound according to claim 1, wherein
A is phenyl, pyridyl, isothiazolyl, thiazolyl, or thiophenyl, optionally substituted with 1 or 2 residues selected independently from F, Cl, methoxy, methyl, NC—, $CF_3O$— and $CF_3$;
R1 is $R^{10}$—C(O)—, $R^{11}$—$(C_nH_{2n})$—, isopropyl, tert-butyl or $CH_3$—$SO_2$—, wherein n is 1, 2 or 3;
R2 is OH or methoxy;
R3 is H or methyl;
R4 and R5 are H;
R6 is H;
R7 and R8 are independently selected from H, F, Cl and Br;
R9 is H, F, Cl, Br, NC—, methyl, ethyl, cyclopropyl, methoxy, ethoxy, methyl-S—, ethyl-S— or $CF_3$;
R10 is methyl, ethyl, n-propyl, isopropyl, n-butyl, isobutyl, tert-butyl, cyclopropyl, methoxy or methoxymethyl-;
R11 is H, cyclopropyl, methoxy or $CF_3$;
or a stereoisomer or stereoisomeric mixture thereof, or a pharmaceutically acceptable salt thereof.

5. A compound according to claim 1, selected from the group consisting of
3-[1-((1R,2R)-4,6-Difluoro-2-hydroxy-indan-1-yl)-5-propionyl-4,5,6,7-tetrahydro-1H-pyrazolo[4,3-c]pyridin-3-yl]-benzonitrile;
3-[5-Cyclopropanecarbonyl-1-((1R,2R)-4,6-difluoro-2-hydroxy-indan-1-yl)-4,5,6,7-tetrahydro-1H-pyrazolo[4,3-c]pyridin-3-yl]-benzonitrile;
1-[1-((1R,2R)-4,6-Difluoro-2-hydroxy-indan-1-yl)-3-(3-trifluoromethoxy-phenyl)-1,4,6,7-tetrahydro-pyrazolo[4,3-c]pyridin-5-yl]-ethanone;
1-[3-(3-Chloro-phenyl)-1-((1S,2S)-4,6-difluoro-2-hydroxy-indan-1-yl)-1,4,6,7-tetrahydro-pyrazolo[4,3-c]pyridin-5-yl]-ethanone;
1-[1-((1R,2R)-4,6-Difluoro-2-hydroxy-indan-1-yl)-3-(2-fluoro-5-methoxy-phenyl)-1,4,6,7-tetrahydro-pyrazolo[4,3-c]pyridin-5-yl]-ethanone;
3-[5-Acetyl-1-((1R,2R)-4-bromo-6-fluoro-2-hydroxy-indan-1-yl)-4,5,6,7-tetrahydro-1H-pyrazolo[4,3-c]pyridin-3-yl]-benzonitrile;
3-[5-Acetyl-1-((1R,2R)-6-fluoro-2-hydroxy-4-methyl-indan-1-yl)-4,5,6,7-tetrahydro-1H-pyrazolo[4,3-c]pyridin-3-yl]-benzonitrile;
1-[1-((1R,2R)-4,6-Difluoro-2-hydroxy-indan-1-yl)-3-(6-trifluoromethyl-pyridin-2-yl)-1,4,6,7-tetrahydro-pyrazolo[4,3-c]pyridin-5-yl]-ethanone;
3-[5-Cyclopropanecarbonyl-1-((1R,2R)-4,6-difluoro-2-hydroxy-indan-1-yl)-4,5,6,7-tetrahydro-1H-pyrazolo[4,3-c]pyridin-3-yl]-benzamide;
3-[1-((1R,2R)-4,6-Difluoro-2-hydroxy-indan-1-yl)-5-isobutyryl-4,5,6,7-tetrahydro-1H-pyrazolo[4,3-c]pyridin-3-yl]-benzonitrile;
3-(3-Cyano-phenyl)-1-((1R,2R)-4,6-difluoro-2-hydroxy-indan-1-yl)-1,4,6,7-tetrahydro-pyrazolo[4,3-c]pyridine-5-carboxylic acid methyl ester;
1-[1-((1R,2R)-4,6-Difluoro-2-hydroxy-indan-1-yl)-3-(4-fluoro-3-trifluoromethyl-phenyl)-1,4,6,7-tetrahydro-pyrazolo[4,3-c]pyridin-5-yl]-ethanone;
3-[5-Acetyl-1-((1R,2R)-4,6-dichloro-2-hydroxy-indan-1-yl)-4,5,6,7-tetrahydro-1H-pyrazolo[4,3-c]pyridin-3-yl]-benzonitrile;
1-[1-((1S,2S)-4,6-Difluoro-2-hydroxy-indan-1-yl)-3-(3-trifluoromethyl-phenyl)-1,4,6,7-tetrahydro-pyrazolo[4,3-c]pyridin-5-yl]-ethanone;

racemic 1-[1-((1S,2S)-4,6-Difluoro-2-hydroxy-2-methyl-indan-1-yl)-3-(4-fluoro-3-trifluoromethyl-phenyl)-1,4,6,7-tetrahydro-pyrazolo[4,3-c]pyridin-5-yl]-ethanone;

3-[1-((1R,2R)-4,6-Difluoro-2-hydroxy-indan-1-yl)-5-(3,3,3-trifluoro-propyl)-4,5,6,7-tetrahydro-1H-pyrazolo[4,3-c]pyridin-3-yl]-benzamide;

3-[5-Acetyl-1-((1R,2R)-4-chloro-6-fluoro-2-hydroxy-indan-1-yl)-4,5,6,7-tetrahydro-1H-pyrazolo[4,3-c]pyridin-3-yl]-benzonitrile;

3-[5-Acetyl-1-((1R,2R)-6-chloro-4-fluoro-2-hydroxy-indan-1-yl)-4,5,6,7-tetrahydro-1H-pyrazolo[4,3-c]pyridin-3-yl]-benzonitrile;

1-[1-((1R,2R)-4,6-Difluoro-2-hydroxy-indan-1-yl)-3-(3-methoxy-phenyl)-1,4,6,7-tetrahydro-pyrazolo[4,3-c]pyridin-5-yl]-ethanone;

3-[5-Acetyl-1-((1R,2R)-4,6-difluoro-2-methoxy-indan-1-yl)-4,5,6,7-tetrahydro-1H-pyrazolo[4,3-c]pyridin-3-yl]-benzonitrile;

1-[(S)-3-(4-Fluoro-phenyl)-1-indan-1-yl-1,4,6,7-tetrahydro-pyrazolo[4,3-c]pyridin-5-yl]-ethanone;

1-[1-((1R,2R)-4,6-Difluoro-2-hydroxy-indan-1-yl)-3-(4-fluoro-phenyl)-1,4,6,7-tetrahydro-pyrazolo[4,3-c]pyridin-5-yl]-ethanone;

3-[5-Acetyl-1-((1R,2R)-4-cyclopropyl-6-fluoro-2-hydroxy-indan-1-yl)-4,5,6,7-tetrahydro-1H-pyrazolo[4,3-c]pyridin-3-yl]-benzonitrile;

(1R,2R)-1-[5-Cyclopropylmethyl-3-(4-fluoro-phenyl)-4,5,6,7-tetrahydro-pyrazolo[4,3-c]pyridin-1-yl]-4,6-difluoro-indan-2-ol;

Propionic acid (1R,2R)-1-[3-(3-cyano-phenyl)-5-propionyl-4,5,6,7-tetrahydro-pyrazolo[4,3-c]pyridin-1-yl]-4,6-difluoro-indan-2-yl ester;

1-[1-((1R,2R)-4,6-Dichloro-2-hydroxy-indan-1-yl)-3-(6-trifluoromethyl-pyridin-2-yl)-1,4,6,7-tetrahydro-pyrazolo[4,3-c]pyridin-5-yl]-ethanone;

(1R,2R)-4,6-Difluoro-1-[3-(4-fluoro-phenyl)-5-(2-methoxy-ethyl)-4,5,6,7-tetrahydro-pyrazolo[4,3-c]pyridin-1-yl]-indan-2-ol;

1-[1-((1R,2R)-6-Chloro-4-fluoro-2-hydroxy-indan-1-yl)-3-(4-fluoro-phenyl)-1,4,6,7-tetrahydro-pyrazolo[4,3-c]pyridin-5-yl]-ethanone;

1-[1-((1R,2R)-4,6-Difluoro-2-hydroxy-indan-1-yl)-3-(4-trifluoromethyl-phenyl)-1,4,6,7-tetrahydro-pyrazolo[4,3-c]pyridin-5-yl]-ethanone;

(1R,2R)-4,6-Difluoro-1-[3-(4-fluoro-phenyl)-5-propyl-4,5,6,7-tetrahydro-pyrazolo[4,3-c]pyridin-1-yl]-indan-2-ol;

3-[5-Acetyl-1-((1S,2S)-4,6-difluoro-2-hydroxy-indan-1-yl)-4,5,6,7-tetrahydro-1H-pyrazolo[4,3-c]pyridin-3-yl]-benzonitrile;

3-[5-Acetyl-1-((1R,2R)-6-chloro-2-hydroxy-indan-1-yl)-4,5,6,7-tetrahydro-1H-pyrazolo[4,3-c]pyridin-3-yl]-benzonitrile;

1-[(R)-3-(4-Fluoro-phenyl)-1-indan-1-yl-1,4,6,7-tetrahydro-pyrazolo[4,3-c]pyridin-5-yl]-ethanone;

3-[1-((1R,2R)-4,6-Difluoro-2-hydroxy-indan-1-yl)-5-(2-methoxy-acetyl)-4,5,6,7-tetrahydro-1H-pyrazolo[4,3-c]pyridin-3-yl]-benzonitrile;

1-[1-((1R,2R)-4,6-Difluoro-2-hydroxy-indan-1-yl)-3-(3-trifluoromethyl-phenyl)-1,4,6,7-tetrahydro-pyrazolo[4,3-c]pyridin-5-yl]-ethanone;

1-[1-((1S,2S)-4,6-Difluoro-2-hydroxy-indan-1-yl)-3-(3-trifluoromethoxy-phenyl)-1,4,6,7-tetrahydro-pyrazolo[4,3-c]pyridin-5-yl]-ethanone;

1-[1-((1R,2R)-6-Chloro-2-hydroxy-indan-1-yl)-3-(4-fluoro-phenyl)-1,4,6,7-tetrahydro-pyrazolo[4,3-c]pyridin-5-yl]-ethanone;

3-[5-Cyclopropylmethyl-1-((1R,2R)-4,6-difluoro-2-hydroxy-indan-1-yl)-4,5,6,7-tetrahydro-1H-pyrazolo[4,3-c]pyridin-3-yl]-benzonitrile;

3-[5-Acetyl-1-((1R,2R)-4-ethyl-6-fluoro-2-hydroxy-indan-1-yl)-4,5,6,7-tetrahydro-1H-pyrazolo[4,3-c]pyridin-3-yl]-benzonitrile;

3-[1-((1R,2R)-4,6-Difluoro-2-hydroxy-indan-1-yl)-5-(2-methoxy-ethyl)-4,5,6,7-tetrahydro-1H-pyrazolo[4,3-c]pyridin-3-yl]-benzonitrile;

3-[5-Acetyl-1-((1R,2R)-6-fluoro-2-hydroxy-4-methylsulfanyl-indan-1-yl)-4,5,6,7-tetrahydro-1H-pyrazolo[4,3-c]pyridin-3-yl]-benzonitrile;

3-[5-Acetyl-1-((1R,2R)-4,6-difluoro-2-hydroxy-indan-1-yl)-4,5,6,7-tetrahydro-1H-pyrazolo[4,3-c]pyridin-3-yl]-benzonitrile;

3-[1-((1R,2R)-4,6-Difluoro-2-hydroxy-indan-1-yl)-5-(3,3,3-trifluoro-propyl)-4,5,6,7-tetrahydro-1H-pyrazolo[4,3-c]pyridin-3-yl]-benzamide;

3-[1-((1R,2R)-4,6-Difluoro-2-hydroxy-indan-1-yl)-5-(2,2-dimethyl-propionyl)-4,5,6,7-tetrahydro-1H-pyrazolo[4,3-c]pyridin-3-yl]-benzonitrile;

racemic 1-[1-((1R,2R)-5,6-Dichloro-2-hydroxy-indan-1-yl)-3-(4-fluoro-phenyl)-1,4,6,7-tetrahydro-pyrazolo[4,3-c]pyridin-5-yl]-ethanone;

1-[1-((1R,2R)-4,6-Difluoro-2-methoxy-indan-1-yl)-3-(4-fluoro-phenyl)-1,4,6,7-tetrahydro-pyrazolo[4,3-c]pyridin-5-yl]-ethanone;

1-[3-(3-Chloro-phenyl)-1-((1R,2R)-4,6-difluoro-2-hydroxy-indan-1-yl)-1,4,6,7-tetrahydro-pyrazolo[4,3-c]pyridin-5-yl]-ethanone;

racemic 3-[5-Acetyl-1-((1R,2R)-4,6-difluoro-2-hydroxy-2-methyl-indan-1-yl)-4,5,6,7-tetrahydro-1H-pyrazolo[4,3-c]pyridin-3-yl]-benzonitrile;

1-[1-((1R,2R)-4,6-Difluoro-2-hydroxy-indan-1-yl)-3-p-tolyl-1,4,6,7-tetrahydro-pyrazolo[4,3-c]pyridin-5-yl]-ethanone;

1-[1-((1R,2R)-4,6-Difluoro-2-hydroxy-indan-1-yl)-3-(4-fluoro-3-methoxy-phenyl)-1,4,6,7-tetrahydro-pyrazolo[4,3-c]pyridin-5-yl]-ethanone;

5-[5-Acetyl-1-((1R,2R)-4,6-difluoro-2-hydroxy-indan-1-yl)-4,5,6,7-tetrahydro-1H-pyrazolo[4,3-c]pyridin-3-yl]-2-fluoro-benzonitrile;

1-[1-((1R,2R)-4,6-Difluoro-2-hydroxy-indan-1-yl)-3-(3-fluoro-phenyl)-1,4,6,7-tetrahydro-pyrazolo[4,3-c]pyridin-5-yl]-ethanone;

1-[3-(4-Chloro-phenyl)-1-((1R,2R)-4,6-difluoro-2-hydroxy-indan-1-yl)-1,4,6,7-tetrahydro-pyrazolo[4,3-c]pyridin-5-yl]-ethanone;

racemic 1-[1-((1R,2R)-5,7-Dichloro-2-hydroxy-indan-1-yl)-3-(4-fluoro-phenyl)-1,4,6,7-tetrahydro-pyrazolo[4,3-c]pyridin-5-yl]-ethanone;

1-[1-((1R,2R)-4,6-Difluoro-2-hydroxy-indan-1-yl)-3-(4-methoxy-phenyl)-1,4,6,7-tetrahydro-pyrazolo[4,3-c]pyridin-5-yl]-ethanone;

(1R,2R)-4,6-Difluoro-1-[3-(4-fluoro-phenyl)-5-isopropyl-4,5,6,7-tetrahydro-pyrazolo[4,3-c]pyridin-1-yl]-indan-2-ol;

(1R,2R)-1-[5-Acetyl-3-(3-cyano-phenyl)-4,5,6,7-tetrahydro-pyrazolo[4,3-c]pyridin-1-yl]-6-fluoro-2-hydroxy-indan-4-carbonitrile; and 3-[1-((1R,2R)-4,6-Dichloro-2-hydroxy-indan-1-yl)-5-methanesulfonyl-4,5,6,7-tetrahydro-1H-pyrazolo[4,3-c]pyridin-3-yl]-benzonitrile;

or a stereoisomer thereof, or a pharmaceutically acceptable salt thereof.

6. A pharmaceutical composition comprising a compound according to claim 1 or a pharmaceutically acceptable salt thereof and a pharmaceutically acceptable carrier or additive.

7. A method for the treatment of neurodegenerative disorders, the method comprising administering to a patient in need thereof an effective dose of a compound of formula I or a pharmaceutically acceptable salt thereof according to any one of claims 1 to 5.

8. A method for the treatment of arrhythmias in a patient in need thereof, comprising administering to the patient a compound of formula I or a pharmaceutically acceptable salt thereof according to any one of claims 1 to 5.

9. A method for the treatment of sleep-related respiratory disorders, central and obstructive sleep apneas, upper airway resistance syndrome, Cheyne-Stokes respiration, snoring, postoperative hypoxia and apnea, muscle-related respiratory disorders, respiratory disorders after long-term mechanical ventilation (weaning), respiratory disorders during adaptation in high mountains, or chronic lung disorders with hypoxia and hypercapnia in a patient in need thereof, comprising administering a compound formula I or a pharmaceutically acceptable salt thereof according to any one of claims 1 to 5.

10. A method for the treatment of respiratory depression associated with anesthesia or procedural sedations for small interventions or for diagnostic purposes in a patient in need thereof, comprising administering a compound of formula I or a pharmaceutically acceptable salt thereof according to any one of claims 1 to 5.

11. A method for the treatment of respiratory depression by opioids in chronic pain treatment in a patient in need thereof, comprising administering a compound of formula I or a pharmaceutically acceptable salt thereof according to any one of claims 1 to 5.

12. A method for the treatment of multiple sclerosis or inflammatory or degenerative disorders of the central nervous system in a patient in need thereof, comprising administering a compound of formula I or a pharmaceutically acceptable salt thereof according to any one of claims 1 to 5.

13. A method for the preparation of a compound according to claim 1, comprising the reaction of 4,5,6,7-tetrahydro-1H-pyrazolo[4,3-c]pyridine 3 with epoxide 6 or 10 for the preparation of 2-hydroxy-indan-1-yl-substituted 4,5,6,7-tetrahydro-1H-pyrazolo[4,3-c]pyridine 11, by heating a mixture of 4,5,6,7-tetrahydro-1H-pyrazolo[4,3-c]pyridine 3 and epoxide 6 or 10 in the presence of an excess of a base in an inert solvent, or by deprotonation of 4,5,6,7-tetrahydro-1H-pyrazolo[4,3-c]pyridine 3 with a base and alkylating with epoxide 6 or 10:

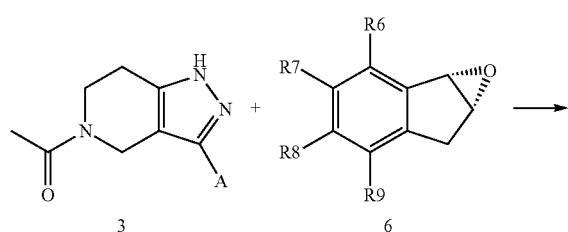

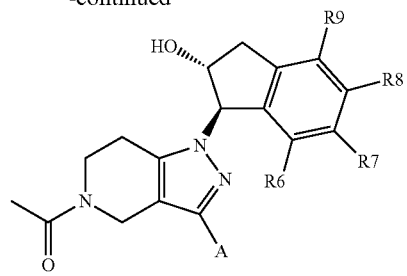

11

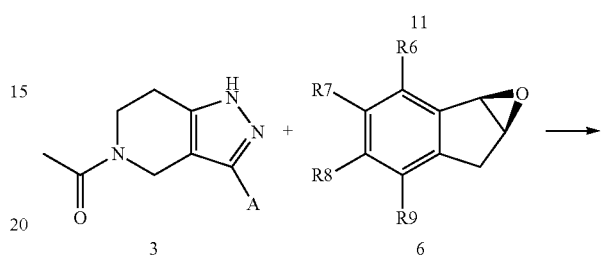

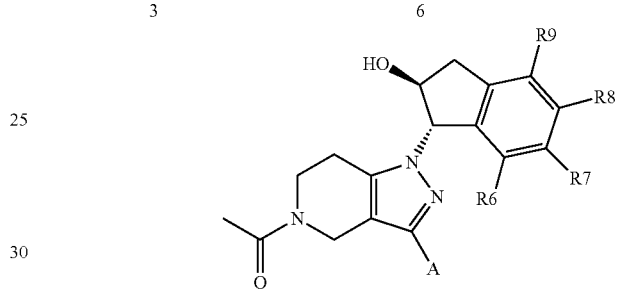

11

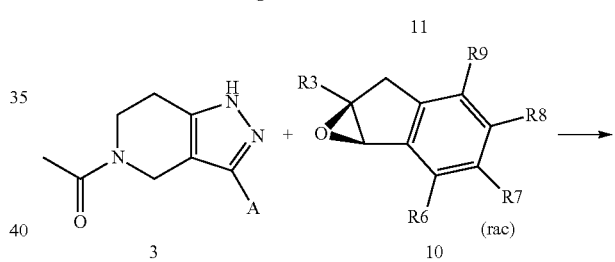

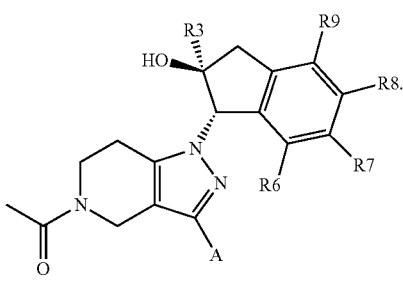

11

14. A method for the preparation of a compound of claim 1, comprising the reaction of 4,5,6,7-tetrahydro-1H-pyrazolo[4,3-c]pyridine 3 with aminoindan-1-ol 4' or 8' for the preparation of compound 12, by heating a mixture of 4,5,6,7-tetrahydro-1H-pyrazolo[4,3-c]pyridine 3 and aminoindan-1-ol 4' or 8' in the presence of a phosphine and a 1,1'-(azodicarbonyl) compound:

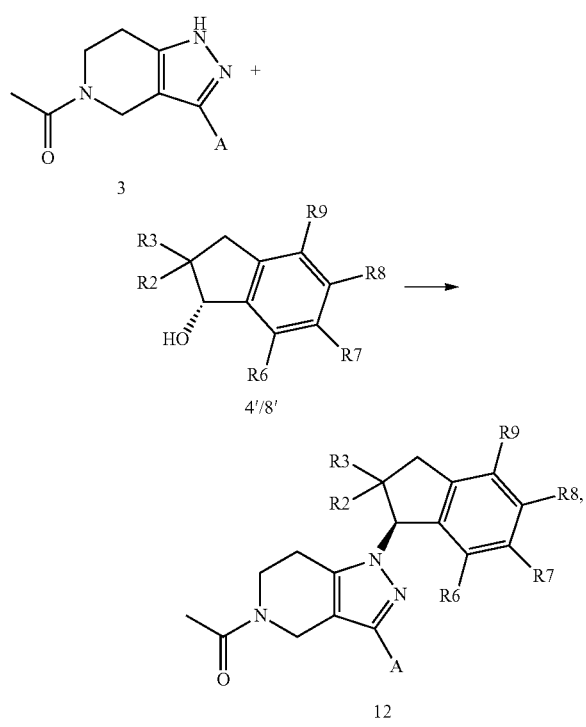

wherein R2 is H, $(C_1-C_6)$-alkyl, $(C_1-C_6)$-alkyloxy- or $(C_1-C_6)$-alkyl-C(O)O—.

15. A pharmaceutical composition comprising a compound according to claim 5 or a pharmaceutically acceptable salt thereof and a pharmaceutically acceptable carrier or additive.

16. The method of claim 8, wherein the arrhythmia is atrial tachyarrhythmia, atrial fibrillation or atrial flutter.

17. The method of claim 11, wherein the chronic pain treatment is related to cancer, palliative care or procedural sedations.

18. A method for inhibiting TASK-1 in a patient in need thereof, comprising administering a compound of formula I or a pharmaceutically acceptable salt thereof, according to claim 1.

19. A method for inhibiting TASK-1 in a cell, comprising contacting the cell with a compound of formula I or a pharmaceutically acceptable salt thereof, according to claim 1.

20. The method of claim 18, wherein the administration is intravenous administration, oral administration, nasal administration, intramuscular administration, subcutaneous administration, inhalative administration, topical administration or pharyngeal administration.

21. A method for weaning from longterm mechanical ventilation, in a patient in need thereof, comprising administering a compound of formula I or a pharmaceutically acceptable salt thereof according to claim 1.

* * * * *